United States Patent
Kuzma et al.

(10) Patent No.: US 8,507,432 B2
(45) Date of Patent: *Aug. 13, 2013

(54) CONTROLLED RELEASE FORMULATIONS OF OCTREOTIDE

(75) Inventors: Petr Kuzma, Princeton, NJ (US); Stephanie Decker, Princeton, NJ (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 394 days.

This patent is subject to a terminal disclaimer.

(21) Appl. No.: 12/814,293

(22) Filed: Jun. 11, 2010

(65) Prior Publication Data

US 2010/0317579 A1    Dec. 16, 2010

Related U.S. Application Data

(60) Division of application No. 12/240,690, filed on Sep. 29, 2008, now Pat. No. 7,803,773, which is a continuation of application No. 11/372,749, filed on Mar. 10, 2006, now Pat. No. 7,452,868.

(60) Provisional application No. 60/660,930, filed on Mar. 11, 2005.

(51) Int. Cl.
*A61K 38/31* (2006.01)

(52) U.S. Cl.
USPC .......... 514/11.1; 424/422; 424/461; 424/462; 526/329.7

(58) Field of Classification Search
None
See application file for complete search history.

(56) References Cited

U.S. PATENT DOCUMENTS

| | | |
|---|---|---|
| 2,168,331 A | 8/1939 | Fields et al. |
| 2,265,226 A | 12/1941 | Clewell et al. |
| 2,513,014 A | 6/1950 | Fields |
| 3,772,435 A | 11/1973 | Wilbur |
| 3,921,632 A | 11/1975 | Bardani |
| 3,975,350 A | 8/1976 | Hudgin et al. |
| 4,131,604 A | 12/1978 | Szycher |
| 4,285,987 A | 8/1981 | Ayer et al. |
| 4,298,002 A | 11/1981 | Ronel et al. |
| 4,386,039 A | 5/1983 | Szycher |
| 4,523,005 A | 6/1985 | Szycher |
| 4,743,673 A | 5/1988 | Johnston et al. |
| 4,751,133 A | 6/1988 | Szycher et al. |
| 4,846,793 A | 7/1989 | Leonard et al. |
| 4,871,094 A | 10/1989 | Gall et al. |
| 4,954,587 A | 9/1990 | Mueller |
| 4,959,217 A | 9/1990 | Sanders et al. |
| 4,994,028 A | 2/1991 | Leonard et al. |
| 5,004,614 A | 4/1991 | Staniforth |
| 5,035,891 A | 7/1991 | Runkel et al. |
| 5,254,662 A | 10/1993 | Szycher et al. |
| 5,266,325 A | 11/1993 | Kuzma et al. |
| 5,273,752 A | 12/1993 | Ayer et al. |
| 5,292,515 A | 3/1994 | Moro et al. |
| 5,342,622 A | 8/1994 | Williams et al. |
| 5,354,835 A | 10/1994 | Blair |
| 5,428,123 A | 6/1995 | Ward et al. |
| 5,431,921 A | 7/1995 | Thombre |
| 5,443,505 A | 8/1995 | Wong et al. |
| 5,464,933 A | 11/1995 | Bolognesi et al. |
| 5,468,811 A | 11/1995 | Moro et al. |
| 5,538,739 A | 7/1996 | Bodmer et al. |
| 5,614,223 A | 3/1997 | Sipos |
| 5,637,309 A | 6/1997 | Tajima et al. |
| 5,686,411 A | 11/1997 | Gaeta et al. |
| 5,688,530 A | 11/1997 | Bodmer et al. |
| 5,756,127 A | 5/1998 | Grisoni et al. |
| 5,817,343 A | 10/1998 | Burke |
| 5,854,127 A | 12/1998 | Pan |
| 5,876,761 A | 3/1999 | Bodmer et al. |
| 5,894,458 A | 4/1999 | Takizawa et al. |
| 6,087,334 A | 7/2000 | Beeley et al. |
| 6,143,718 A | 11/2000 | Kolterman et al. |
| 6,159,490 A | 12/2000 | Deghenghi |
| 6,313,254 B1 | 11/2001 | Meijs et al. |
| 6,337,318 B1 | 1/2002 | Trigg et al. |
| 6,361,797 B1 | 3/2002 | Kuzma et al. |
| 6,417,164 B1 | 7/2002 | Kolterman et al. |
| 6,579,851 B2 | 6/2003 | Goeke et al. |

(Continued)

FOREIGN PATENT DOCUMENTS

| | | |
|---|---|---|
| EP | 0 246 653 A2 | 11/1987 |
| EP | 0 314 206 | 5/1989 |
| EP | 0384 646 | 2/1990 |
| EP | 0 551 699 A1 | 7/1993 |
| EP | 0 645 136 A2 | 3/1995 |
| FR | 821383 | 4/1937 |
| FR | 821383 A | 12/1937 |
| GB | 1 306 541 A | 2/1973 |
| JP | 05-269759 | 10/1993 |
| JP | 05-269760 A | 10/1993 |

(Continued)

OTHER PUBLICATIONS

Trainer, Peter J. et al; "Treatment of acromegaly with the growth hormone receptor antagonist pegvisomant." N. Engl. J. Med. (2000) 342(16) p. 1171-1177.*
Eugster, Erica A. and Pescovitz, Ora H. "Gigantism." J. Clin. Endocrinol. Metabol. (1999) 84(12) p. 4379-4384.*
U.S. Appl. No. 12/490,971, filed Jun. 24, 2009, Kuzma et al.
U.S. Appl. No. 12/490,979, filed Jun. 24, 2009, Kuzma et al.
Higuchi, et al., *Pro-Drugs as Novel Drug Delivery Systems: A.C.S Symposium Series*, American Chemical Society, Washington, DC, 1975.

(Continued)

*Primary Examiner* — Cecilia J Tsang
*Assistant Examiner* — Fred Reynolds
(74) *Attorney, Agent, or Firm* — RatnerPrestia

(57) ABSTRACT

A formulation of octreotide or pharmaceutically acceptable salts thereof, which provides controlled release of a therapeutically effective amount of octreotide for a period of at least about two months. Methods of treating acromegaly, decreasing growth hormone, decreasing IGF-1, and treating conditions associated with carcinoid tumors and VIPomas by administering a controlled release formulation of octreotide are provided herein.

20 Claims, 12 Drawing Sheets

(56) References Cited

U.S. PATENT DOCUMENTS

| | | | |
|---|---|---|---|
| 6,602,694 | B1 | 8/2003 | Albrandt et al. |
| 6,770,623 | B1 | 8/2004 | Chang et al. |
| 6,872,700 | B1 | 3/2005 | Young et al. |
| 6,942,264 | B1 | 9/2005 | Mendez |
| 6,969,480 | B2 | 11/2005 | Dalton et al. |
| 7,008,927 | B2 | 3/2006 | Ochiai et al. |
| 7,056,887 | B2 | 6/2006 | Coolidge et al. |
| 7,101,853 | B2 | 9/2006 | Young et al. |
| 7,105,489 | B2 | 9/2006 | Hathaway |
| 7,115,569 | B2 | 10/2006 | Beeley et al. |
| 7,118,737 | B2 | 10/2006 | Kochendoerfer et al. |
| 7,153,825 | B2 | 12/2006 | Young et al. |
| 7,220,721 | B1 | 5/2007 | Beeley et al. |
| 7,259,136 | B2 | 8/2007 | Hathaway et al. |
| 7,271,238 | B2 | 9/2007 | Gaeta et al. |
| 7,452,868 | B2 * | 11/2008 | Kuzma et al. .................. 514/1.1 |
| 7,759,312 | B2 * | 7/2010 | Kuzma et al. .................. 514/1.1 |
| 7,803,773 | B2 | 9/2010 | Kuzma et al. |
| 7,960,335 | B2 * | 6/2011 | Kuzma et al. .................. 514/1.1 |
| 2002/0141985 | A1 | 10/2002 | Pittner et al. |
| 2003/0036504 | A1 | 2/2003 | Kolterman et al. |
| 2003/0162862 | A1 | 8/2003 | McCabe et al. |
| 2004/0002454 | A1 | 1/2004 | Coolidge et al. |
| 2004/0071736 | A1 | 4/2004 | Quinn et al. |
| 2004/0097419 | A1 | 5/2004 | Petersen et al. |
| 2005/0037078 | A1 | 2/2005 | Kuo et al. |
| 2005/0079216 | A1 | 4/2005 | Petereit et al. |
| 2005/0143303 | A1 | 6/2005 | Quay et al. |
| 2005/0287320 | A1 | 12/2005 | Dalton et al. |
| 2006/0019903 | A1 | 1/2006 | Kuzma et al. |
| 2006/0030528 | A1 | 2/2006 | Hathaway et al. |
| 2006/0035836 | A1 | 2/2006 | Coolidge et al. |
| 2006/0067911 | A1 | 3/2006 | Nilsson et al. |
| 2006/0122106 | A1 | 6/2006 | Gedulin et al. |
| 2006/0148713 | A1 | 7/2006 | Beeley et al. |
| 2006/0204540 | A1 | 9/2006 | Kuzma et al. |
| 2006/0233747 | A1 | 10/2006 | Kochendoerfer et al. |
| 2006/0293232 | A1 | 12/2006 | Levy et al. |
| 2007/0010656 | A1 | 1/2007 | Beeley et al. |
| 2007/0037897 | A1 | 2/2007 | Wang et al. |
| 2008/0311170 | A1 | 12/2008 | Kuzma et al. |
| 2009/0035343 | A1 | 2/2009 | Kuzma et al. |
| 2009/0087470 | A1 | 4/2009 | Kuzma et al. |
| 2011/0009338 | A1 | 1/2011 | Kuzma et al. |

FOREIGN PATENT DOCUMENTS

| | | |
|---|---|---|
| JP | 07-097338 A | 4/1995 |
| JP | 07-252166 A | 10/1995 |
| JP | 11-506730 T | 6/1999 |
| JP | 2002-535452 T | 10/2002 |
| NZ | 245383 | 5/1994 |
| WO | WO-96/40049 A1 | 12/1996 |
| WO | WO-98/44964 | 10/1998 |
| WO | WO-00/44356 A1 | 8/2000 |
| WO | WO-02/49573 A2 | 6/2002 |
| WO | WO-02/078597 A2 | 10/2002 |
| WO | WO-2004/071736 A2 | 8/2004 |
| WO | WO-2005/013936 A2 | 2/2005 |
| WO | WO-2005/041873 A2 | 5/2005 |
| WO | WO-2006/099288 A3 | 9/2006 |
| WO | WO-2007/028394 | 3/2007 |
| WO | WO-2008/061355 A1 | 5/2008 |
| WO | WO-2008/134475 A2 | 11/2008 |

OTHER PUBLICATIONS

Roche, ed., *Bioreversible Carriers in Drug Design: Theory and Application*, Pergamon Press, New York, 1987.

Berge, et al., "Pharmaceutical Salts," *Journal of Pharmaceutical Sciences*, vol. 66, No. 1, Jan. 1977, pp. 1-19.

Eurasian Patent Office Decision on Patentability corresponding to EU 200701956/28, dated Jan. 21, 2009, 6 pages.

New Zealand Patent Office Examination Report corresponding to NZ 561400, dated Jul. 28, 2009, 2 pages.

Chinese Office Action corresponding to CN 2006800160292, dated Sep. 4, 2009, 8 pages.

"RxMed: Pharmaceutical Information-Sandostatin LAR DEPOT" [online], Jan. 6, 2003 [retrieved Aug. 16, 2006]; http://www.rxmed.com.

A.R. Gennaro, Remington: The Science and Practice of Pharmacy, 19th Edition, p. 1662.

Bevan et al., Primary Medical Therapy for Acromegaly: An Open, Prospective, Multicenter Study of the Effects of Subcutaneous and Intramuscular Slow-Release Octreotide on Growth Hormone, Insulin-Like Growth Factor-L, and Tumor Size, J. Clin. Endoc. Metab,. 87(10), 2002, pp. 4554-4563.

Chertin et al., "An Implant Releasing the Gonadotropin Hormone-Releasing Hormone Agonist Histrelin Maintains Medical Castration for Up to 30 Months in Metastic Prostate Cancer," Journal of Urology,Baltimore,MD,US,vol. 163.

International Search Report and Written Opinion, PCT/US2009/050215, dated Nov. 25, 2009, 11 pgs.

International Search Report, PCT/US00/01664, dated Jul. 13, 2000, 1 pg.

International Search Report, PCT/US2006/08891, dated Dec. 4, 2006, 2 pgs.

International Search Report, PCT/US2005/021368, dated Oct. 23, 2006, 3 pgs.

International Search Report, PCT/US2008/061511, dated Nov. 8, 2009, 2 pgs.

Lan NaLee, "Volume of Blood in a Human," from http://hypertextbook.com/facts/1998/LanNaLee.shtml, (1998) updated (2001).

Langer, "Implantable Controlled Release Systems," Pharmac. Ther. (1983), vol. 21, p. 35-51.

P. Kuzma et al., U.S. PTO Office Action, U.S. Appl. No. 11/155,822 dated Jan. 22, 2008, 12 pgs.

P. Kuzma et al., U.S. PTO Office Action, U.S. Appl. No. 11/155,822 dated Feb. 18, 2009, 11 pgs.

P. Kuzma et al., U.S. PTO Office Action, U.S. Appl. No. 11/155,822 dated Oct. 13, 2009, 21 pgs.

Schlegel et al., "Effective Long-Term Androgen Suppression in Men with Prostate Cancer Using a Hydrogel Implant with the GnRH Agonist Histrelin," Urology,vol. 58.

Barradell, L. B. et al., "Histrelin: A Review of its Pharmacological Properties and Therapeutic Role in Central Precocious Puberty," Drugs, vol. 45, No. 4, Apr. 1993, pp. 570-588; published by Adis International Limited.

English Translation of Examiner's Final Decision of Rejection for Japanese Appln. No. 2008-501025 dated Dec. 1, 2009.

Feuillan, P. P. et al., "Follow-up of children and young adults after GnRH-agonist therapy for central precocious puberty," J. Endocrinol. Invest., vol. 24, 2001, pp. 734-736; published by Editrice Kurtis.

First Notice of Reasons for Rejection and translation received for Japanese Appln. No. 2000-595660 dated Jun. 9, 2009.

International Search Report and Written Opinion for PCT/US2009/050215 dated Nov. 25, 2009.

International Search Report and Written Opinion for PCT/US2009/048484 dated Nov. 26, 2009.

Kim, S. W., et al., "Water in Polymers—Solute Permeation Through Hydrogel Membranes," ACS Symposium Series, 127 (1980), pp. 347-359.

Nielsen, P. E., et al., "Peptide Nucleic Acid (PNA). A DNA Mimic with a Peptide Backbone," Bioconjugate Chem., vol. 5, No. 1, 1994, pp. 3-7.

Non-final Office Action received for U.S. Appl. No. 11/372,749 dated Feb. 5, 2008.

Notice of Allowance received for U.S. Appl. No. 11/372,749 dated Aug. 11, 2008.

Palii, et al., "Medical treatment of diabetic retinopathy with somatostatin analogues," Expert Opinion Investig. Drugs, vol. 16, No. 1, (2007), pp. 73-82.

Pawlikowski, et al., "Perspectives of new potential therapeutic applications of somatostatin analogs," Neuroendocrinology Letters, vol. 24, Nos. 1/2, Feb.-Apr. 2003, pp. 21-27.

Pierard-Franchimont, et al., "Incidental Control of Rosacea by Somatostatin," Dermatology, (2003) 206:249-251.

Refojo, M. F., et al., "Microscopic Desterimination of the Penetration of Proteins and Polysaccharides into Poly(hydroxyethyl Methacrylate) and similar Hydrogels," Journal of Polymer Science, Polymer Symposium, vol. 66, (1979), pp. 227-237.

American Peptide Company, Inc., Peptide Catalog 2006-2007, pp. 119, 171, 175, 211, 217, 219, 227, 296, 315, 317 and 329.

Bodmer D., et al: "Factors influencing the release of peptides and proteins from biodegradable parenteral depot systems" Journal of Controlled Release, Elsevier, Amsterdam, NL LNKD-DOI:10.1016/0168-3659(92)90014-I, vol. 21, No. 1-3, Jul. 1, 1992, pp. 129-137, XP025702099 ISSN: 0168-3659 [retrieved on Jul. 1, 1992].

European Search Report for EP/00904513, completed Mar. 27, 2003.

European Search Report for EP/92300394, completed Sep. 28, 1992.

European Search Report for EP/92300395, dispatched Feb. 27, 1995.

International Search Report for PCT/US2009/048475, dated Jun. 1, 2010.

Non-final Office Action for U.S. Appl. No. 12/490,979, mail date Sep. 29, 2010.

Non-final Office Action for U.S. Appl. No. 11/372,749, mail date Feb. 5, 2008.

Notice of Allowance for U.S. Appl. No. 12/240,690, mail date Mar. 26, 2010.

Notice of Allowance for U.S. Appl. No. 12/171,999, mail date Mar. 22, 2010.

Office Action for U.S. Appl. No. 07/589,957, mail date Oct. 17, 1991.

Final Office Action for U.S. Appl. No. 11/155,822, mail date Jul. 8, 2010.

Non-final Office Action for U.S. Appl. No. 12/490,971, mail date Sep. 14, 2010.

Remington's Pharmaceutical Sciences, Osol., A. ed., Mack Publishing Co., (1980).

Spitz, et al. "GnRH Superanalog Implants for Prostate Cancer" Proceedings of the 12th International Congress of Endocrinology, 2004, pp. 389-395.

Supplementary European Search Report for EP/67838004, completed Jun. 23, 2010.

Non-final Office Action received for U.S. Appl. No. 12/109,852 dated Oct. 6, 2011.

Notice of Allowance on U.S. Appl. No. 12/490,971 dated Jun. 9, 2011.

International Preliminary Report on Patentability received for PCT/US2009/048475 dated Jan. 5, 2011.

Non-final Office Action received for U.S. Appl. No. 11/155,822 dated Mar. 4, 2011.

Notice of Allowance received for U.S. Appl. No. 12/490,979 dated Feb. 4, 2011.

Shi et al., Expert Opin. Drug Deliv., "Current Advances in Sustained-Release Systems for Parenteral Drug Delivery," vol. 2(6), 2005, pp. 1039-1058.

O' Donnell, Luke J. and Farthing, Michael J.G., "Therapeutic potential of long acting somatostatin analogue in gastrointestinal diseases," Gut, 1989,(30) 1165-1172.

Prommer Eric E., Established and potential therapeutic applications of octreotide in palliative care, Support Care Cancer 2008 (16) 1117-1123.

Examination Report received for New Zealand Application No. 561400 dated Dec. 16, 2009.

Higuchi, T., "Mechanism of sustained-action medication." J. Pharma Sci. (1963) 52 (12) p. 1145-1149.

Final Office Action received for U.S. Appl. No. 12/814,276 dated Jan. 8, 2013.

Non-Final Office Action received for U.S. Appl. No. 12/814,276 dated Sep. 10, 2012.

Non-Final Office Action received for U.S. Appl. No. 12/814,286 dated Oct. 10, 2012.

Non-Final Office Action received for U.S. Appl. No. 12/814,286 dated Feb. 6, 2013.

International Search Report for PCT International Application No. PCT/US2009/048475 dated Jun. 1, 2010.

European Search Report for Application No. EP92300395 dated Sep. 28, 1992.

Chinese Office action for Application No. 200980135776.1 dated May 10, 2013.

Final Office Action for U.S. Appl. No. 12/814,286 dated Jun. 3, 2013.

* cited by examiner

CONTROLLED RELEASE FORMULATIONS OF OCTREOTIDE

CROSS REFERENCE TO RELATED APPLICATIONS

This application is a divisional patent application of U.S. patent application Ser. No. 12/240,690, filed on Sep. 29, 2008, which is a continuation of U.S. patent application Ser. No. 11/372,749, filed on Mar. 10, 2006, which claims the benefit of U.S. Provisional Application No. 60/660,930, filed Mar. 11, 2005, the entire contents of which are incorporated herein by reference.

FIELD OF THE INVENTION

This invention relates generally to an octreotide pharmaceutical composition that can be used to treat individuals affected with hormonal disorders. The present invention is preferably formulated as a controlled release formulation.

Acromegaly is a hormonal disorder that results when the pituitary gland produces excess growth hormone (GH). It most commonly affects middle-aged adults and can result in serious illness and premature death. Once recognized, acromegaly is treatable in most patients, but because of its slow and often insidious onset, it frequently is not diagnosed correctly.

The present invention may be utilized to treat a variety of hormonal disorders, including acromegaly and gigantism. One of its most common symptoms is the abnormal growth of the hands and feet. Gradually, bony changes alter the patient's facial features: the brow and lower jaw protrude, the nasal bone enlarges, and spacing of the teeth increases. Overgrowth of bone and cartilage often leads to arthritis. When tissue thickens, it may trap nerves, causing carpal tunnel syndrome, characterized by numbness and weakness of the hands. Other symptoms of acromegaly include thick, coarse, oily skin; skin tags; enlarged lips, nose and tongue; deepening of the voice due to enlarged sinuses and vocal cords; snoring due to upper airway obstruction; excessive sweating and skin odor; fatigue and weakness; headaches; impaired vision; abnormalities of the menstrual cycle and sometimes breast discharge in women; and impotence in men. There may be enlargement of body organs, including the liver, spleen, kidneys and heart.

The most serious health consequences of acromegaly are diabetes mellitus, hypertension, and increased risk of cardiovascular disease. Patients with acromegaly are also at increased risk for polyps of the colon that can develop into cancer.

When GH-producing tumors occur in childhood, the disease that results is called gigantism rather than acromegaly. Fusion of the growth plates of the long bones occurs after puberty so that development of excessive GH production in adults does not result in increased height. Prolonged exposure to excess GH before fusion of the growth plates causes increased growth of the long bones and increased height.

Acromegaly is caused by prolonged overproduction of GH by the pituitary gland. The pituitary is a small gland at the base of the brain that produces several important hormones to control body functions such as growth and development, reproduction, and metabolism. GH is part of a cascade of hormones that, as the name implies, regulates the physical growth of the body. This cascade begins in a part of the brain called the hypothalamus, which makes hormones that regulate the pituitary. One of these, growth hormone-releasing hormone (GHRH), stimulates the pituitary gland to produce GH. Another hypothalamic hormone, somatostatin, inhibits GH production and release. Secretion of GH by the pituitary into the bloodstream causes the production of another hormone, called insulin-like growth factor 1 (IGF-1), in the liver. IGF-1 is the factor that actually causes the growth of bones and other tissues of the body. IGF-1, in turn, signals the pituitary to reduce GH production. GHRH, somatostatin, GH, and IGF-1 levels in the body are tightly regulated by each other and by sleep, exercise, stress, food intake and blood sugar levels. If the pituitary continues to make GH independent of the normal regulatory mechanisms, the level of IGF-1 continues to rise, leading to bone growth and organ enlargement. The excess GH also causes changes in sugar and lipid metabolism and can cause diabetes.

In over 90% of acromegaly patients, the overproduction of GH is caused by a benign tumor of the pituitary gland, called an adenoma. These tumors produce excess GH and, as they expand, compress surrounding brain tissues, such as the optic nerves. This expansion causes the headaches and visual disturbances that are often symptoms of acromegaly. In addition, compression of the surrounding normal pituitary tissue can alter production of other hormones, leading to changes in menstruation and breast discharge in women and impotence in men.

In some patients, acromegaly is caused not by pituitary tumors but by tumors of the pancreas, lungs, and adrenal glands. These tumors also lead to an excess of GH, either because they produce GH themselves or, more frequently, because they produce GHRH, the hormone that stimulates the pituitary to make GH. In these patients, the excess GHRH can be measured in the blood and establishes that the cause of the acromegaly is not due to a pituitary defect. When these non-pituitary tumors are surgically removed, GH levels fall and the symptoms of acromegaly improve.

Treatment regimens include reducing GH production to normal levels to relieve the pressure that the growing pituitary tumor exerts on the surrounding brain areas, to preserve normal pituitary function, and to reverse or ameliorate the symptoms of acromegaly. Currently, treatment options include surgical removal of the tumor, drug therapy, and radiation therapy of the pituitary.

SUMMARY OF THE INVENTION

Octreotide is one drug used to treat acromegaly. Octreotide exerts pharmacologic actions similar to those of the natural hormone somatostatin. Octreotide decreases GH and IGF-1 levels, as well as glucagons and insulin. Octreotide also suppresses luteinizing hormone (LH) response to gonadotropin releasing hormone (GnRH), decreases splanchnic blood flow, and inhibits the release of serotonin, gastrin, vasoactive intestinal peptide, secretin, motilin, and pancreatic polypeptide. In many patients, GH levels fall within one hour and headaches improve within minutes after the injection of octreotide. Several studies have shown that octreotide is effective for long-term treatment. Octreotide also has been used successfully to treat patients with acromegaly caused by non-pituitary tumors. In some acromegaly patients who already have diabetes, octreotide can reduce the need for insulin and improve blood sugar control.

Octreotide is currently available as Sandostatin LAR® Depot, which is, upon reconstitution, a suspension of microspheres containing octreotide acetate. Sandostatin LAR® Depot is the only medication indicated for the long-term maintenance therapy in acromegalic patients. It is also indicated for the long-term treatment of severe diarrhea and flushing episodes associated with metastatic carcinoid tumors and profuse water diarrhea associated with VIP-secreting tumors.

Sandostatin LAR® Depot is administered via intramuscular injection every four weeks, following a titration period. Octreotide acetate has also been available in an immediate-release formulation, Sandostatin® Injection solution, which was required to be administered by injection three times daily.

The present invention provides a therapeutically effective amount of octreotide over an extended period of time, preferably at least about two months, more preferably about six months and up to about two years. The present invention also provides compositions that provide controlled release of octreotide over at least about two months, preferably about six months, and up to about two years.

Embodiments of the present invention relate to a pharmaceutical composition comprising octreotide or salts, prodrugs or derivatives thereof, which can be used in the effective treatment of various diseases and conditions, including, but not limited to acromegaly, diabetes, severe diarrhea and flushing episodes associated with carcinoid tumors and watery diarrhea associated with VIPomas.

In one embodiments of the present invention, a composition including a hydrogel and octreotide is provided. The octreotide may be present as a free base, salt or complex form. The composition is capable of providing, upon administration to a patient, a desirable pharmacokinetic profile of octreotide for the condition being treated.

Another embodiment of the present invention is directed to a pharmaceutical composition containing octreotide for implantation into a patient. In one embodiment, the implantable composition may further comprise a hydrogel, which provides consistent, predetermined, and controlled release of octreotide upon subcutaneous implantation under the skin of a patient. Preferably hydrogels include methacrylate based polymers and polyurethane based polymers.

Another embodiment of the present invention is a stable pharmaceutical composition which comprises a therapeutically effective amount of octreotide in an implant that provides a pharmacokinetic profile of the octreotide to a patient that has a desired $C_{ss}$ over an extended period of time. The composition may be used to establish and or maintain in a patient, a therapeutically effective level of octreotide. Preferably octreotide is released over time so that a therapeutically effective level of octreotide in the patient can be achieved over at least about two months, and more preferably about six months or longer. In a more preferred embodiment, undesirable spikes or peaks in the release of octreotide are avoided. In preferred embodiments, the pharmaceutical composition comprises octreotide, more preferably octreotide acetate, contained within a hydrogel. In another preferred embodiment, the pharmaceutical composition comprises octreotide, more preferably octreotide acetate, contained within polyurethane based polymers, a methacrylate based polymer. The pharmaceutical composition of the present invention may also comprise one or more pharmaceutically acceptable excipients.

Another embodiment of the present invention is a stable, controlled release implantable formulation of a composition which includes a therapeutically effective amount of octreotide contained in a polymer reservoir that provides a pharmacokinetic release profile of octreotide in the blood plasma of the patient extending over a period of at least about two months, and more preferably about six months or longer.

Preferably, the implantable formulation of the composition is an implant formed by polymerization of hydrophilic monomers of the present invention. In preferred embodiments, the implantable formulation includes a hydrophilic implant of a therapeutically effective amount of octreotide, such as octreotide acetate, contained within hydrophilic copolymers, such as 2-hydroxyethyl methacrylate (HEMA) and hydroxypropyl methacrylate (HPMA). The implant form of the present invention may also include one or more pharmaceutically acceptable excipients. In a further embodiment, the implantable formulation of the composition is an implant formed from polyurethane based polymers.

The octreotide formulations of the present invention impart chemical and physical stability to the composition while providing a controlled release profile. This enhanced stability is most notably observed in compositions and dosage forms of the present invention where the stability of octreotide is achieved while maintaining the desired controlled-release profile. Specifically, the implantable formulations of the present invention exhibit superior resistance to moisture absorption, while providing a release profile of octreotide that permits establishment of a therapeutically effective concentration of octreotide over an extended period of time, preferably at least two months, more preferably about six months and up to about two years.

In one embodiment of the present invention, a controlled release formulation comprising octreotide that provides an in vivo average $C_{ss}$ of about 0.1 ng/ml to about 9 ng/ml, more preferably about 1 ng/ml to about 2 ng/ml, of octreotide in a patient is provided. In one embodiment, the formulation contains from about 20 to about 150 milligrams of octreotide, more preferably, about 40 to about 90 milligrams of octreotide. The formulation may be selected from an implant, a pump, or other similar controlled release device. In preferred embodiments, the formulation releases a therapeutically effective amount of octreotide over a period of about two months to about two years, more preferably about six months to about one year, more preferably about six months.

In further embodiments, the controlled release formulation of octreotide may comprise a hydrophilic copolymer. Preferred hydrophilic copolymers include 2-hydroxyethyl methacrylate and hydroxypropyl methacrylate. In one embodiment, the copolymer comprises about 20% of 2-hydroxyethyl methacrylate and about 80% hydroxypropylmethacrylate. The formulation may further comprise magnesium stearate. In another embodiment, the formulation may further comprise hydroxypropylcellulose.

In another embodiment, the controlled release formulation of octreotide may comprise a polyurethane based polymer.

In another embodiment, a method of treating a patient comprising administering a controlled release formulation of octreotide is provided. In one preferred embodiment, the controlled release formulation maintains an in vivo average $C_{ss}$ of about 0.1 ng/ml to about 9 ng/ml of octreotide in a patient in need thereof.

Another embodiment of the present invention is a method of treating acromegaly or symptoms associated with acromegaly comprising administering a controlled release formulation of octreotide is provided. Preferably, the controlled release formulation is capable of maintains an average $C_{max}$ average of said octreotide at about 0.1 ng/ml to about 4 ng/ml for an extended period of time. Preferably the extended period of time is about two months to about two years, more preferably about six months.

In a further embodiment, a method of treating acromegaly or symptoms associated with acromegaly comprising administering at least one hydrogel implant comprising between about 40 to about 90 milligrams of octreotide, more preferably about 50 milligrams, more preferably about 83 milligrams, is provided. In certain methods, one hydrogel implant may be administered and in other methods two or more hydrogel implants may be administered. The hydrogel implant(s) may administered every about two months to about two years, preferably about every six months.

A further embodiment of the present invention is a therapeutic composition comprising a hydrophilic copolymer and octreotide. In one embodiment, the octreotide may be released at a rate to maintain a $C_{ss}$ of about 0.1 ng/ml to about 9 ng/ml over at least two months to about twenty-four months. In one embodiment the hydrophilic copolymer comprises a mixture of an ethylenically unsaturated hydrophilic monomer A and an ethylenically unsaturated hydrophilic monomer B. One preferred monomer A is 2-hydroxyethyl methacrylate. In one embodiment, the hydrophilic copolymer may comprise from about 15% to about 70%, more preferably about 20%, of the hydrophilic copolymer. One preferred monomer B is hydroxypropylmethacrylate. In one embodiment, the hydrophilic copolymer may comprise about 80% of the hydrophilic copolymer. Such therapeutic compositions are capable of release at a rate to maintain a $C_{ss}$ of octreotide of about 1 ng/ml to about 2 ng/ml over at least two months to about twenty-four months.

A further embodiment of the present invention provides an implantable drug delivery device comprising octreotide, wherein said device delivers a therapeutically effective amount of octreotide over at least about two months to about twenty-four months. In one embodiment, the therapeutically effective amount of octreotide is from about 20 μg to about 800 μg per day. In another embodiment, the therapeutically effective amount of octreotide is from about 30 μg to about 300 μg per day.

Another embodiment of the present invention is a controlled release formulation comprising octreotide for implantation, said formulation including octreotide in a hydrophilic polymer effective to permit release of said octreotide at a rate of about 30 μg to about 250 μg per day, more preferably about at an average rate of about 100 μg per day in vitro, over about six months in vitro.

A controlled release formulation comprising octreotide for implantation, said formulation including octreotide in a hydrophilic polymer effective to permit in vitro release of: no more than about 20% of said octreotide from said formulation after about 6 weeks; and about 60% of said octreotide from said formulation after about six months.

In another embodiment of the present invention, an implant comprising octreotide, HEMA, HPMA is provided. The implant may further comprise pharmaceutically acceptable excipients, including, for example, hydroxypropylcellulose and/or magnesium stearate.

The compositions of the present invention may be used in the treatment of a condition in a patient which includes establishing a therapeutically effective concentration of octreotide in the patient in need thereof. The compositions may be used for building up a level and or maintaining a therapeutically effective concentration of octreotide in the patient by administration, preferably implantation, of the composition every about six months. The compositions of the present invention may be formulated to avoid large peaks in initial release of octreotide. The compositions of the present invention when administered to a patient in need thereof provide for the treatment of hormonal diseases that are characterized by increased levels of GH or IGF-1. In addition, the compositions of the present invention when administered to a patient in need thereof provide for the treatment of symptoms associated with carcinoid tumors and VIPomas. Preferably, the compositions are a stable, controlled release implant containing a therapeutically effective amount of octreotide in a hydrogel, preferably methacrylate or polyurethane based polymers, such that a therapeutically effective blood plasma level of octreotide is maintained in the patient for a period of at least about 2 months, preferably at least about 6 months, more preferably about 12 months and up to two years.

DETAILED DESCRIPTION OF THE INVENTION

Figure 1:
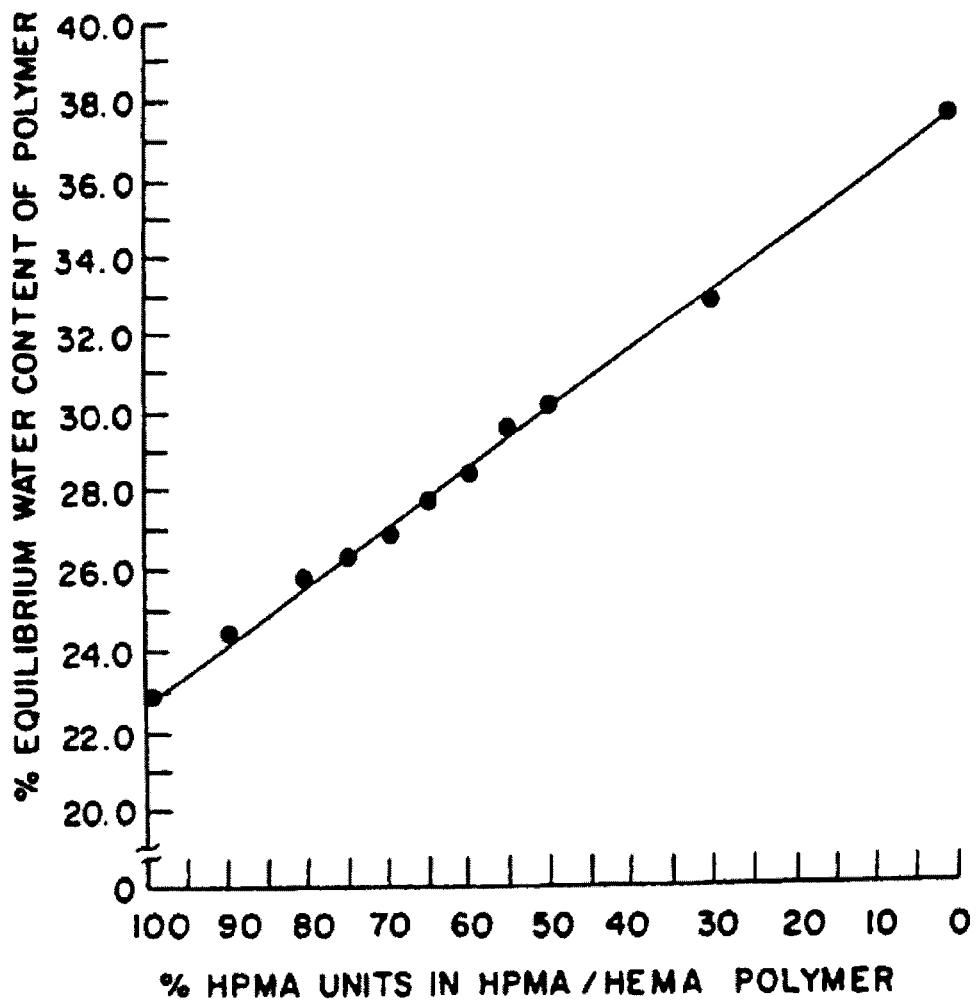
FIG. 1 is a graph showing the linear relationship between the equilibrium water content vs. the weight percent content of hydroxypropyl methacrylate (HPMA) units in crosslinked HEMA/HPMA polymers at their maximum state of hydration.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims. The terms used herein have meanings recognized and known to those of skill in the art, however, for convenience and completeness, particular terms and their meanings are set forth below.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference to the extent they support the present invention. Nothing herein is to be construed as an admission that the invention is not entitled to antedate such disclosure by virtue of prior invention.

As used herein, the term "about" means plus or minus 10% of the numerical value of the number with which it is being used. For example, about 50% means in the range of 45%-55%.

"Controlled release formulation" refers to a formulation designed to consistently release a predetermined, therapeutically effective amount of drug or other active agent such as a polypeptide or a synthetic compound over an extended period of time, with the result being a reduction in the number of treatments necessary to achieve the desired therapeutic effect. In the matter of the present invention, a controlled formulation would decrease the number of treatments necessary to achieve the desired effect in terms of decreased growth hormone levels or decreased IGF-1 levels, or an improvement in symptoms associated with acromegaly, including but not limited to abnormal growth. The controlled release formulations of the present invention achieve a desired pharmacokinetic profile in a subject, preferably commencement of the release of the active agent substantially immediately after placement in a delivery environment, followed by consistent, sustained, preferably zero-order or near zero-order release of the active agent.

The terms "patient" and "subject" mean all animals including humans. Examples of patients or subjects include humans, cows, dogs, cats, goats, sheep, and pigs.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetraethylammonium, methlyamine, dimethylamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.).

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount sufficient to decrease, prevent, or ameliorate the symptoms associated with a medical condition. In the context of hormonal therapy it can also mean to normalize body functions or hormone levels in disease or disorders. For example, a therapeutically effective amount of a controlled release formulation of octreotide is a predetermined amount calculated to achieve the desired effect, e.g., to effectively decrease growth hormone or IGF-1 levels in a patient.

Octreotide is an octapeptide with the following amino acid sequence: L-cysteinamide, D-phenylalanyl-L-cysteiny-L-phenylalanyl-D-tryptophyl-L-lysyl-L-threonyl-N-[2-hydroxy-1-(hydroxymethyl)propyl]-,cyclic (2→7)-disulfide; [R—(R*,R*)]. The structure of octreotide is shown below.

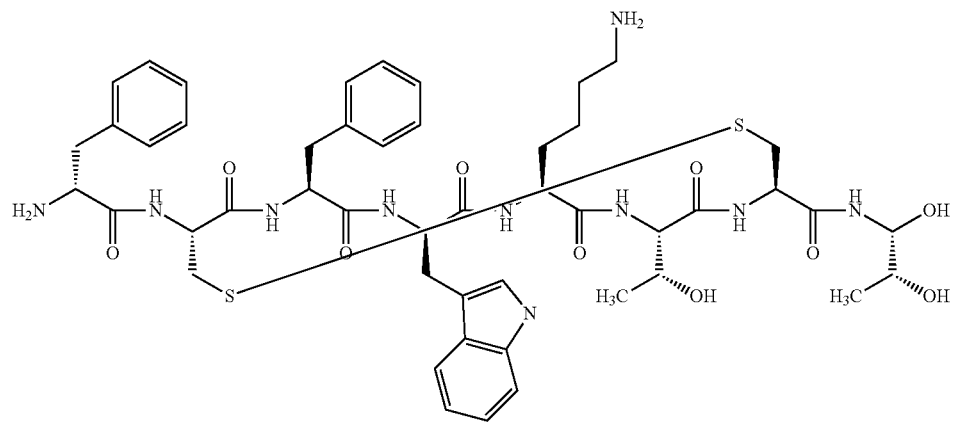

Octreotide

The chemical formula is $C_{49}H_{66}N_{10}O_{10}S_2$ and its molecular weight is 1019.3 Da. Its therapeutic category is gastric antisecretory agent. The octreotide of the present invention may exist in e.g., free form, salt form or in the form of complexes thereof. Acid addition salts may be formed with e.g. organic acids, polymeric acids and inorganic acids. Acid addition salts include e.g., the hydrochloride and acetates. Complexes are e.g., formed from octreotide on addition of inorganic substances, e.g., inorganic salts or hydroxides such as Ca- and Zn-salts and/or addition of polymeric organic substances. The acetate salt is the preferred salt for formulations of the present invention.

Embodiments of the present invention provide a drug delivery device that can achieve the following objectives: a controlled release rate (zero order release rate) to maximize therapeutic effects and minimize unwanted side effects; an easy way to retrieve the device if it is necessary to end the treatment; an increase in bioavailability with less variation in absorption and no first pass metabolism.

One aspect of the invention is a controlled release pharmaceutical composition comprising octreotide acetate in a controlled release hydrogel device. The composition of the present invention is capable of providing, upon administration to a patient, a release profile of octreotide extending over at least 2 months, preferably at least about 6 months or more, up to about two years. Preferably octreotide is contained within the hydrogel and the formulation releases a therapeutically effective amount of octreotide over an extended period of time. In preferred embodiments, the hydrogel comprises a polymer selected from methacrylate based polymers, polyurethane based polymers and combinations thereof. A therapeutically effective amount is an amount of octreotide, preferably octreotide acetate, that when administered to a patient or subject, ameliorates a symptom of acromegaly. In a preferred embodiment, the formulation may further include pharmaceutically acceptable excipients.

When the compositions of the present invention are administered to a patient, the concentration of octreotide in the patient's plasma over time (release profile) may extend over a period of at least 2 months, preferably about 6 months, and up to about two years. The compositions may provide a mean plasma concentration at steady state of octreotide in a human patient of from about 0.1 to about 9 ng/ml, preferably about 1 to about 2 ng/ml, more preferably about 1.2 to about 1.6 ng/ml. Steady state is the point at which the amount of drug administered over a dosing interval equals the amount of drug being eliminated over that same period.

The hydrogel may be a homogeneous homopolymer or copolymer having a predetermined equilibrium water content (EWC) value formed by the polymerization of a mixture of ethylenically unsaturated monomer A and ethylenically unsaturated monomer B, for example, 2-hydroxyethyl methacrylate (HEMA) and hydroxypropyl methacrylate (HPMA). The predetermined EWC may be calculated by determining the EWC values of the hydrogel homopolymer of hydrophilic monomer A (homopolymer A) and the hydrogel homopolymer of hydrophilic monomer B (homopolymer B); determining the relationship of the EWC values of the homogeneous copolymers AB versus the chemical composition of said copolymers AB; selecting the targeted EWC value and determining the chemical composition of copolymer AB having the targeted EWC value; forming a polymerizable mixture of monomer A and monomer B in amounts sufficient to yield copolymer AB having the targeted EWC value; and effect the polymerization reaction to yield copolymer AB characterized by the targeted EWC value.

By the expressions "copolymer AB" or "copolymer AB consists essentially of monomer A units and monomer B units" is meant that the addition copolymerization of monomer A and monomer B has been effected through the polymerizable ethylenic bond of the said monomers. By way of illustration, if monomer A is 2-hydroxyethyl methacrylate and monomer B is N-methylacrylamide, copolymer AB contains recurring monomer A units and recurring monomer B units.

Unless the context indicates otherwise, the term "copolymer" includes polymers made by polymerizing a mixture of at least two ethylenically unsaturated monomers.

By the term "HEMA unit(s)" is meant the structure

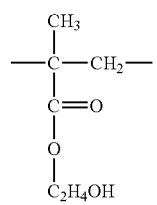

recurring in the polymer obtained by polymerizing hydrophilic material containing 2-hydroxyethyl methacrylate ("HEMA").

By the term "HPMA unit(s)" is meant the structure

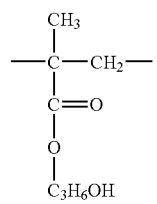

obtained by polymerizing hydrophilic material containing hydroxypropyl methacrylate ("HPMA").

Liquid polymerizable material useful in the hydrophilic products include a wide variety of polymerizable hydrophilic, ethylenically unsaturated compounds, in particular, hydrophilic monomers such as the monoester of an acrylic acid or methacrylic acid with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Acrylic and methacrylic acid can also be useful in these formulations.

Mixtures of hydrophilic monomers are employed in the polymerization reaction. The type and proportion of monomers are selected to yield a homogeneous polymer, preferably a crosslinked homogeneous polymer, which on hydration possesses the desired EWC value for the contemplated application or use. This value can be predetermined by preparing a series of copolymers using different monomer ratios, e.g., mixtures of HEMA and HPMA of varying ratios, ascertaining the EWC values of the copolymers, and plotting the relationship of % HPMA (or % HEMA) units in the HPMA/HEMA copolymers versus weight percent EWC of the copolymers (see FIG. 1).

In one embodiment, the hydrophilic implant as a xerogel, readily absorbs water. In a hydrated state it is referred to as a hydrogel. In either form, it is biocompatible and non-toxic to the host and non-biodegradable. It is, of course, water-swellable and water-insoluble. When the hydrogel attains its maximum level of hydration, the water content of the hydrogel is referred to as "equilibrium water content". The percent water content of the hydrogel (any state of hydration) is determined as follows:

$$\frac{\text{weight of hydrogel} - \text{weight of dry polymer(xerogel)}}{\text{weight of hydrogel}} \times 100$$

In some instances the polymerization of certain hydrophilic monomeric mixtures may result in homogeneous hydrophilic copolymers which dissolve, to a varying extent, in an aqueous medium. In such cases, a small amount, e.g., up to 3 percent, of a copolymerizable polyethylenically unsaturated crosslinking agent can be included in the monomeric mixture to obtain homogeneous crosslinked copolymers which are water-insoluble as well as water-swellable. Slightly crosslinked homopolymer of HEMA has a EWC value of about 38%. Crosslinked copolymers of HEMA and HPMA have EWC values below 38%. On the other hand, crosslinked copolymers of HEMA and acrylamide exhibit EWC values above 38 w/v %, e.g., upwards to approximately 75 weight %, and higher. Therefore, depending on the useful or effective elution rate of the active compound, e.g., drug, that is required of a hydrogel delivery system for a particular application, one skilled in the art, by following the teachings disclosed herein, can tailor-make copolymer hydrogel membranes which will elute the drug at the required rate. Preferred copolymers contain about 15% to about 70 weight % of HEMA units and from about 85 to 30 weight % of units of a second ethylenic monomer and possess predetermined EWC values in the range of from about 20% to about 75%, preferably about 25%. Highly preferred homogenous copolymers are those made from hydrophilic monomeric mixtures containing from about 80 weight % HPMA, and from about 20 weight % HEMA. In further embodiments, the mixture may further contain a small amount of a polyethylenically unsaturated crosslinking agent, e.g., trimethylolpropane trimethacrylate ("TMPTMA").

Various aspects of the invention include homogeneous hydrophilic copolymers whose homogeneous polymer structure is formed via the polymerization of a mixture of hydrophilic monomers described previously; and the drug delivery device which utilize the homogeneous polymer cartridges in the delivery system. The polymerization of a mixture of hydrophilic monomers and hydrophobic monomers yields heterogeneous polymers. When hydrophobic segments are present in the polymer, the interfacial free energy increases, thus enhancing protein adsorption and mineralization after implantation in an animal. Hydrogels of polyHEMA were measured to have interfacial free energy close to zero. According to the interfacial free energy interpretation, hydrogels of strictly hydrophilic components would strongly appear to be biocompatible with body tissue. Slightly crosslinked polyHEMA is a homogeneous, hydrophilic "homopolymer" (disregarding the relatively small quantities of polymerized crosslinking agent therein) of relatively fixed characteristics or values. Techniques of altering the "homopolymer" polyHEMA to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor-made properties.

Useful crosslinking agents which can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate; and the di-, tri- and tetra-acrylate or methacrylate esters of the following polyols: triethanolamine, glycerol, pentaerythritol, 1,1,1-trimethylolpropane and others.

The polymerization reaction can be carried out in bulk or with an inert solvent. Suitable solvents include water; organic solvents such as water-soluble lower aliphatic monohydric alcohols as well as polyhydric alcohols, e.g., glycol, glycerine, dioxane, etc.; and mixtures thereof.

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates. Illustrative examples include cumene hydroperoxide, t-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one which is effective at moderately low temperature such as at about 20°-80° C., such as tert-butyl peroctoate, benzoyl peroxide, and di(secbutyl) peroxydicarbonate. A conventional redox polymerization catalyst can also be employed. Preferably, polymerization of the ethylenic compounds can be effected using radiation, e.g., U.V., X-Ray, gamma radiation, microwave, or other well-know forms of radiation. A preferred catalyst for U.V. cure is benzoin methyl ether. Catalysts and/or initiators and/or radiation are employed in a catalytically effective amount to optimize the polymerization reaction.

The current invention focuses on the application of polyurethane based polymers, thermoplastics or thermosets, to the creation of implantable drug devices to deliver biologically active compounds at controlled rates for prolonged period of time. Polyurethane polymers are preferably made into cylindrical hollow tubes with one or two open ends through extrusion, (reaction) injection molding, compression molding, or spin-casting (see e.g. U.S. Pat. Nos. 5,266,325 and 5,292,515, herein incorporated by reference in their entireties), depending on the type of polyurethane used.

Thermoplastic polyurethane can be processed through extrusion, injection molding, or compression molding. Thermoset polyurethane can be processed through reaction injection molding, compression molding, or spin-casting. The dimensions of the cylindrical hollow tube are very critical and need to be as precise as possible.

Polyurethane based polymers are synthesized from multifunctional polyols, isocyanates and chain extenders. The characteristics of each polyurethane can be attributed to its structure.

Thermoplastic polyurethanes are made of macrodiols, diisocyanates, and difunctional chain extenders (e.g., U.S. Pat. Nos. 4,523,005 and 5,254,662, herein incorporated by reference in their entireties). Macrodiols make up the soft domains. Diisocyanates and chain extenders make up the hard domains. The hard domains serve as physical crosslinking sites for the polymers. Varying the ratio of these two domains can alter the physical characteristics of the polyurethanes.

Thermoset polyurethanes can be made of multifunctional (greater than difunctional) polyols and/or isocyanates and/or chain extenders (e.g. U.S. Pat. Nos. 4,386,039 and 4,131,604, herein incorporated by reference in their entireties). Thermoset polyurethanes can also be made by introducing unsaturated bonds in the polymer chains and appropriate crosslinkers and/or initiators to do the chemical crosslinking (e.g. U.S. Pat. No. 4,751,133, herein incorporated by reference in its entirety). By controlling the amounts of crosslinking sites and how they are distributed, the release rates of the actives can be controlled.

Different functional groups can be introduced into the polyurethane polymer chains through the modification of the backbones of polyols depending on the properties desired. When the device is used for the delivery of water soluble drugs, hydrophilic pendant groups such as ionic, carboxyl, ether, and hydroxy groups are incorporated into the polyols to increase the hydrophilicity of the polymer (e.g. U.S. Pat. Nos. 4,743,673 and 5,354,835, herein incorporated by reference in their entireties). When the device is used for the delivery of hydrophobic drugs, hydrophobic pendant groups such as alkyl, siloxane groups are incorporated into the polyols to increase the hydrophobicity of the polymer (e.g. U.S. Pat. No. 6,313,254, herein incorporated by reference in its entirety). The release rates of the actives can also be controlled by the hydrophilicity/hydrophobicity of the polyurethane polymers.

In a preferred embodiment, small cylindrically shaped implants contain within their core octreotide, preferably octreotide acetate, and optionally, a pharmaceutically acceptable carrier. The membrane thickness (between the interior and exterior surfaces) of the implant is substantially uniform, and serves as a rate-limiting barrier for the release of the contained agent. Such implants can be plasticized or hydrated and reshaped into other geometrically shaped articles for use in various medical applications.

In the manufacture of the implantable formulation, several factors are considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is well known in the art.

The diffusion coefficient and the water content at which diffusion begins (i.e., below which substantially no diffusion occurs—hereinafter "% $H_d$") are determined. A series of membranes is prepared from various polymers. The membranes are then hydrated to their capacity and their equilibrium water contents are measured. The fully hydrated membranes are placed in the two-compartment, vertical glass cells to measure and plot the diffusion of the macromolecular composition through the membrane materials at the various equilibrium water contents. The equilibrium water content of the most hydrated membrane through which no diffusion is detected (i.e., none of the active agent diffuses into the receptor cell) is the % $H_d$ for the system being tested. This can be accomplished by plotting a curve of the permeability verus equilibrium water content.

The permeability results (diffusion coefficients) are obtained according to Fick's First Law of Diffusion, by use of the equation:

$$dQ/dt = APC/1$$

wherein dQ/dt is the flux through the membrane material (μg/hr); it is measured as the slope of the linear part of the curve of cumulative transport versus time; wherein A is the area of the membrane (cm$^2$); wherein P is the membrane's permeability coefficient (cm$^2$/hr), or DK$_d$, wherein D is the diffusivity of the membrane (cm$^2$/hr), and K$_d$ is the partition coefficient for the membrane/donor solution; wherein 1 is the membrane thickness as measured at the end of the experiment (cm); and wherein C$_d$ is the concentration of the donor solution (μg/cm$^3$).

The release delay profile is then determined. Another series of polymeric membranes can be prepared, again varying the amounts of crosslinker and monomers. These membranes are then hydrated, but only partially, i.e., to a water content less than or equal to % $H_d$. The partially hydrated membranes are placed in two-compartment vertical glass cells to measure and plot the diffusion of the active compound through the membranes versus time. Buffer solutions for the donor and receptor cells may be selected to contact the partially hydrated membranes and further hydrate them at approximately the same rate at which they will hydrate in the delivery environment. The time between commencement of the diffusion study, i.e., addition of the active agent to the donor cell, and the detection of a pharmaceutically effective concentration of the active agent in the receptor cell is the release delay time for that combination of polymer and initial percent hydration.

In order to determine the physical dimensions of the cylindrically-shaped device, the total amount of active agent to be delivered must be determined. This is the product of the desired daily dosage and the duration of delivery. In preferred embodiments, the duration of delivery is at least about 2 months, more preferably about 6 months, and up to about two years. The desired daily dosage is, for example, about 10 to about 1000 μg of octreotide per day, preferably about 20 to about 800 μg of octreotide per day, more preferably about 30 to about 300 μg of octreotide per day.

The volume of the cylindrical reservoir (core) of a cylindrically-shaped device is equal to $\pi r_i^2 h$ wherein $r_i$ is the radius of the reservoir and h is its height. The formula for steady state release from a cylinder is:

$$[dQ/dt] = [2\pi h D K_d C_d]/[\ln(r_o/r_i)]$$

wherein $r_o$ is the outside radius of the cylindrical device; and wherein $C_d$ is the concentration of drug in the donor solution, i.e., the carrier. Steady state release is obtained when $C_d$ is maintained at saturation. The thickness of the membrane needed for the desired sustained release is, therefore, $r_o - r_i$.

The amount of active agent employed will depend not only on the desired daily dose but also on the number of days that dose level is to be maintained. While this amount can be calculated empirically, the actual dose delivered is also a function of any interaction with materials and the carrier, if employed in the device.

Once the appropriate polyurethane polymer is chosen, the next step is to determine the best method to fabricate the cylindrically shaped implants.

For thermoplastic polyurethanes, precision extrusion and injection molding are the preferred choices to produce two open-end hollow tubes with consistent physical dimensions. The reservoir can be loaded freely with appropriate formulations containing actives and carriers or filled with pre-fabricated pellets to maximize the loading of the actives. One open end needs to be sealed first before the loading of the formulation into the hollow tube. To seal the two open ends, two pre-fabricated end plugs may be used. The sealing step can be accomplished through the application of heat or solvent or any other means to seal the ends, preferably permanently.

For thermoset polyurethanes, precision reaction injection molding or spin casting is the preferred choice depending on the curing mechanism. Reaction injection molding is used if the curing mechanism is carried out through heat and spin casting is used if the curing mechanism is carried out through light and/or heat. Preferably, hollow tubes with one open end are made by spin casting. Preferably, hollow tubes with two open ends are made by reaction injection molding. The reservoir can be loaded in the same way as the thermoplastic polyurethanes.

Preferably, to seal an open end, an appropriate light-initiated and/or heat-initiated thermoset polyurethane formulation is used to fill the open end and this is cured with light and/or heat. More preferably, a pre-fabricated end plug can also be used to seal the open end by applying an appropriate light-initiated and/or heat-initiated thermoset polyurethane formulation on to the interface between the pre-fabricated end plug and the open end and cured it with the light and/or heat or any other means to seal the ends, preferably permanently.

The final process involves the conditioning and priming of the implants to achieve the delivery rates required for the actives. Depending upon the types of active ingredient, hydrophilic or hydrophobic, the appropriate conditioning and priming media will be chosen. Water based media are preferred for hydrophilic actives and oil based media are preferred for hydrophobic actives.

To keep the geometry of the device as precise as possible, the preferably cylindrically shaped device can be manufactured through precision extrusion or precision molding process for thermoplastic polyurethane polymers, and reaction injection molding or spin casting process for thermosetting polyurethane polymers.

The cartridge can be made with either one end closed or both ends open. The open end can be plugged with pre-manufactured end plug to ensure a smooth end and a solid seal. The solid actives and carriers can be compressed into pellet form to maximize the loading of the actives.

To identify the location of the implant, radiopaque material can be incorporated into the delivery device by inserting it into the reservoir or by making it into end plug to be used to seal the cartridge.

In various embodiments, the novel formulation of the present invention may contain a pharmaceutically acceptable carrier which may include, but is not limited to, suspending media, solvents, aqueous systems, and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide; liquid glyceryl triesters of a lower molecular weight fatty acid; lower alkanols; glycols; and polyalkylene glycols.

The aqueous systems include, for example, sterile water, saline, dextrose, dextrose in water or saline, and the like. The presence of electrolytes in the aqueous systems may tend to lower the solubility of the macromolecular drug in them.

The solid substrates or matrices include, for example, starch, gelatin, sugars (e.g., glucose), natural gums (e.g., acacia, sodium alginate, carboxymethyl cellulose), and the like. In a preferred embodiment, the pharmaceutical formulation further comprises about 2% to about 20%, more preferably about 10% hydroxypropylcellulose.

The carrier may also contain adjuvants such as preserving, stabilizing, wetting and emulsifying agents, and the like.

The hydrating liquid useful in the practice of the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content."

Once the cartridges are sealed on both ends with filled reservoir, they are conditioned and primed for an appropriate period of time to ensure a constant delivery rate.

The priming and conditioning of the drug delivery devices involves the loading of the actives (drug) into the polymer which surrounds the reservoir, and thus prevent loss of the active before the actual use of the implant. The conditions used for the conditioning and priming step depend on the active, the temperature and the medium in which they are carried out. The conditions for the conditioning and priming may be the same in some instances.

The conditioning and priming step in the process of the preparation of the drug delivery devices is done to obtain a determined rate of release of a specific drug. The conditioning and priming step of the implant containing a hydrophilic drug is preferably carried out in an aqueous medium, more preferably in a saline solution. For hydrophobic drugs, the medium may be a plasma-like medium, including, but not limited to, cyclodextrin. The conditioning and priming steps are carried out by controlling three specific factors namely the temperature, the medium and the period of time.

A person skilled in the art would understand that the conditioning and priming step of the drug delivery device will be affected by the medium in which the device is placed. For example, histrelin and naltrexone implants have been conditioned and primed in saline solution, more specifically, conditioned in saline solution of 0.9% sodium content and primed in saline solution of 1.8% sodium chloride content.

The temperature used to condition and prime the drug delivery device may vary across a wide range of temperatures but, in some instances 37 C., has been preferably used.

The time period used for the conditioning and priming of the drug delivery devices may vary from a single day to several weeks depending on the release rate desired for the specific implant or drug.

A person skilled in the art will understand the steps of conditioning and priming the implants is to optimize the rate of release of the drug contained within the implant. As such, a shorter time period spent on the conditioning and the priming of a drug delivery device results in a lower rate of release of the drug compared to a similar drug delivery device which has undergone a longer conditioning and priming step.

The temperature in the conditioning and priming step will also affect the rate of release in that a lower temperature results in a lower rate of release of the drug contained in the drug delivery device when compared to a similar drug delivery device which has undergone a treatment at a higher temperature.

Similarly, in the case of aqueous solutions, which are in some cases preferably saline solutions, the sodium chloride content of the solution will also determine what type of rate of release will be obtained for the drug delivery device. More specifically, a lower content of sodium chloride would result in a higher rate of release of drug when compared to a drug delivery device which has undergone a conditioning and priming step where the sodium chloride content was higher.

In one embodiment, a pharmaceutical formulation of the present invention comprises a formulation of octreotide acetate within a mixture of HEMA and HPMA copolymer, preferably about 20% HEMA and about 80% HPMA. In preferred embodiments, the pharmaceutical formulation comprises about 20 to about 150 milligrams of octreotide, preferably about 40 to about 90 milligrams. The formulation may further comprise between about 2 to about 20% excipients. In one preferred embodiment, the formulation preferably contains about 10% hydroxypropylcellulose. In another preferred embodiment, the formulation preferably contains about 2% magnesium stearate.

In another embodiment, a pharmaceutical formulation of the present invention comprises a formulation of about 50 milligrams of octreotide within a mixture of HEMA and HPMA copolymer, preferably about 20% HEMA and about 80% HPMA. In a further embodiment, the formulation further comprises about 10% hydroxypropylcellulose and 2% magnesium stearate with the octreotide acetate.

In another embodiment, a pharmaceutical formulation of the present invention comprises a formulation of about 83 mgs of octreotide within a mixture of HEMA and HPMA copolymer, preferably about 40% HEMA and about 60% HPMA. In a further embodiment, the formulation further comprises about 10% hydroxypropylcellulose and 2% magnesium stearate with the octreotide acetate.

In a further embodiment, a pharmaceutical formulation of the present invention comprises a formulation of about 20 milligrams to about 150 milligrams, more preferably about 40 milligrams to about 90 milligrams, of octreotide in a polyurethane based polymer.

A method of treating a disease associated with a hormonal disorder is also provided. The method may include administering octreotide and maintaining a plasma concentration at steady state of octreotide between about 0.1 ng/ml and about 9 ng/ml over an extended period of time, preferably at least about 2 months, and more preferably about 6 months and up to about two years. In preferred embodiment, the plasma concentration at steady state of octreotide is maintained between about 1 ng/ml and about 2 ng/ml, more preferably about 1.2 ng/ml to about 1.6 ng/ml, over an extended period of time. Such hormonal disorders include acromegaly or the like.

One embodiment is a method of decreasing GH levels by administering octreotide and maintaining a steady state plasma concentration of octreotide between about 0.1 ng/ml and about 9 ng/ml, preferably about 1 ng/ml to about 2 ng/ml, more preferably about 1.2 to about 1.6 ng/ml, over an extended period of time, preferably at least about 2 months, and more preferably about 6 months, and up to about two years.

Another embodiment is a method of decreasing IGF-1 levels by administering octreotide and maintaining a plasma concentration of octreotide between about 0.1 ng/ml and about 9 ng/ml, preferably about 1 ng/ml to about 2 ng/ml more preferably about 1.2 to about 1.6 ng/ml, over an extended period of time, preferably at least about 2 months, and more preferably about 6 months, and up to about two years.

Another embodiment is a method of treating acromegaly comprising administering at least one implant of the present invention, preferably two implants, of the present invention. In the method, each implant administered may contain between about 20 to about 150 milligrams of octreotide, preferably about 40 to about 90 milligrams of octreotide, more preferably about 50 milligrams of octreotide, and release a therapeutically effective amount of octreotide over a period of at least two months, preferably about six months, and up to about two years.

Another embodiment is a method of treating symptoms associated with carcinoid tumors and VIPomas. In one embodiment, a method of treating severe diarrhea and flushing episodes associated with carcinoid tumors by administering an implantable formulation of octreotide, which releases a therapeutically effective amount of octreotide over at least about 2 months, preferably about 6 months and up to about two years. In another embodiment, a method of treating watery diarrhea associated with VIPomas by administering an implantable formulation of octreotide, which release a therapeutically effective amount of octreotide over at least about two months, preferably about 6 months and up to about two years.

Another aspect is a therapeutic composition of a hydrogel and octreotide, wherein, upon implantation, the octreotide is released at a rate that provides and/or maintains a $C_{ss}$ of about 0.1 ng/ml to about 9 ng/ml, preferably about 1 ng/ml to about 2 ng/ml, more preferably about 1.2 ng/ml to about 1.6 ng/ml. A further embodiment is a therapeutic composition of a hydrogel and octreotide, wherein, upon implantation, the octreotide is released at a rate of from about 10 µg to about 1000 µg per day over an extended period of time, preferably about 20 µg to about 800 µg, more preferably about 30 µg to about 300 µg per day. In preferred embodiments, the octreotide is release over at least about two months, more preferably about six months, up to about two years. The hydrogel may comprise methacrylate based polymers or polyurethane based polymers.

Another embodiment is a controlled release formulation comprising octreotide and a hydrophilic polymer, which permits release of the octreotide at a rate of about 30 µg to about 250 µg per day over at least about two months, more preferably about six months to about two years in vitro, more preferably about 100 µg to about 130 µg per day. In a further embodiment, the hydrophilic polymer of the formulation permits release of octreotide at an average rate of about 100 µg per day in vitro. Preferably, the hydrophilic polymer is selected from polyurethane based polymers and methacrylate based polymers.

A further embodiment of the present invention is a controlled release formulation comprising octreotide for implantation, wherein the formulation comprises octreotide in a hydrophilic polymer effective to permit in vitro release of no more than about 20% of said octreotide from the formulation after about 6 weeks; and about 60% of said octreotide from said formulation after about six months.

The amount of a pharmaceutically acceptable ocreotide, salt, solvated, or prodrug thereof included in the pharmaceutical composition of the present invention will vary, depending upon a variety of factors, including, for example, the specific octreotide used, the desired dosage level, the type and amount of hydrogel used, and the presence, types and amounts of additional materials included in the composition. The amount of octreotide, or a derivative thereof, in the formulation varies depending on the desired dose for efficient drug delivery, the molecular weight, and the activity of the compound. The actual amount of the used drug can depend on the patient's age, weight, sex, medical condition, disease or any other medical criteria. The actual drug amount is determined according to intended medical use by techniques known in the art. The pharmaceutical dosage formulated according to the invention may be administered about once every six months as determined by the attending physician.

Typically, the octreotide is formulated in the implant or other pharmaceutical composition in amounts of about 20 milligrams to about 150 milligrams, preferably about 40 to about 90 milligrams of octreotide, more preferably about 50 to about 85 milligrams. For adults, the daily dose for treatment of acromegaly is typically about 300 to about 600 µg of immediate release octreotide per day (100 or 200 µg Sandostatin® t.i.d.) Preferably, the amount of octreotide in the composition is formulated to release from about 10 µg to about 1000 µg per day over an extended period of time, preferably about 20 µg to about 800 µg per day, more preferably about 30 µg to about 300 µg per day. Such release rates maintain desired therapeutic levels in the patient's blood at about 0.1 to about 9 ng/ml over an extended period of time.

The hydrogel device in which octreotide is contained provides a controlled release of octreotide into the plasma of the patient. Hydrogels suitable for controlling the release rate of octreotide for use in the pharmaceutical compositions of the present invention include polymers of hydrophilic monomers, including, but not limited to HPMA, HEMA and the like. Such hydrogels are also capable of preventing degradation and loss of octreotide from the composition.

In one embodiment, a pharmaceutical formulation of the present invention comprises octreotide acetate contained within a hydrophilic copolymer of 2-hydroxyethyl methacrylate and hydroxypropyl methacrylate. In a preferred embodiment, the copolymer of the pharmaceutical formulation comprises about 20% HEMA and about 80% HPMA. In another preferred embodiment, the copolymer of the pharmaceutical formulation comprises about 40% HEMA and about 60% HPMA.

In further embodiments, the hydrogel comprises polyurethane based polymers.

The amount of the hydrogel included in the pharmaceutical composition of the present invention will vary depending upon a variety of factors, including, for example, the specific matrix used, its molecular weight, its hydrophilicity, the type and amount of octreotide used, and the presence, types and amounts of additional materials included in the composition.

The size, shape and surface area of the implant may also be modified to increase or decrease the release rate of octreotide from the implant.

The formulations of the present invention exhibit a specific, desired release profile which maximizes the therapeutic effect while minimizing adverse side effects. The desired release profile may be described in terms of the maximum plasma concentration of the drug or active agent ($C_{max}$) and the plasma concentration of the drug or active agent at steady state ($C_{ss}$).

The pharmaceutical composition of the present invention can include also auxiliary agents or excipients, for example, glidants, dissolution agents, surfactants, diluents, binders including low temperature melting binders, disintegrants and/or lubricants. Dissolution agents increase the dissolution rate of octreotide from the dosage formulation and can function by increasing the solubility of octreotide. Suitable dissolution agents include, for example, organic acids such as citric acid, fumaric acid, tartaric acid, succinic acid, ascorbic acid, acetic acid, malic acid, glutaric acid and adipic acid, and may be used alone or in combination. These agents may also be combined with salts of the acids, e.g. sodium citrate with citric acid, in order to produce a buffer system.

Other agents that may alter the pH of the microenvironment on dissolution and establishment of a therapeutically effective plasma concentration profile of octreotide include salts of inorganic acids and magnesium hydroxide. Other agents that may be used are surfactants and other solubilizing materials. Surfactants that are suitable for use in the pharmaceutical composition of the present invention include, for example, sodium lauryl sulphate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters.

Diluents that are suitable for use in the pharmaceutical composition of the present invention include, for example, pharmaceutically acceptable inert fillers such as microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or mixtures thereof. The diluent is preferably a water-soluble diluent. Examples of preferred diluents include, for example: microcrystalline cellulose such as Avicel PH112, Avicel PH101 and Avicel PH102 available from FMC Corporation; lactose such as lactose monohydrate, lactose anhydrous, and Pharmatose DCL 21; dibasic calcium phosphate such as Emcompress available from Penwest Pharmaceuticals; mannitol; starch; sorbitol; sucrose; and glucose. Diluents are carefully selected to match the specific composition with attention paid to the compression properties. The diluent is preferably used in an amount of about 2% to about 80% by weight, preferably about 20% to about 50% by weight, of the controlled release composition.

Glidants are used to improve the flow and compressibility of ingredients during processing. Suitable glidants include, for example, colloidal silicon dioxide, a sub-micron fumed silica that can be prepared by, for example, vapor-phase hydrolysis of a silicon compound such as silicon tetrachloride. Colloidal silicon dioxide is a sub-micron amorphous powder which is commercially available from a number of sources, including Cabot Corporation (under the tradename Cab-O-Sil); Degussa, Inc. (under the tradename Aerosil); and E.I. DuPont & Co. Colloidal silicon dioxide is also known as colloidal silica, fumed silica, light anhydrous silicic acid, silicic anhydride, and silicon dioxide fumed, among others. In one embodiment, the glidant comprises Aerosil 200.

Another agent that may be used is a surfactant, dissolution agent and other solubilizing material. Surfactants that are suitable for use in the pharmaceutical composition of the present invention include, for example, sodium lauryl sulphate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters. Dissolution agents increase the dissolution rate of octreotide and function by increasing the solubility of the octreotide. Suitable dissolution agents include, for example, organic acids such as citric acid, fumaric acid, tartaric acid, succinic acid, ascorbic acid, acetic acid, malic acid, glutaric acid and adipic acid, which may be used alone or in combination. These agents may also be combined with salts of the acids, e.g. sodium citrate with citric acid, in order to produce a buffer system. Other agents that may be used to alter the pH of the microenvironment on dissolution include salts of inorganic acids and magnesium hydroxide.

Disintegrants that are suitable for use in the pharmaceutical composition of the present invention include, for example, starches, sodium starch glycolate, crospovidone, croscarmellose, microcrystalline cellulose, low substituted hydroxypropyl cellulose, pectins, potassium methacrylate-divinylbenzene copolymer, poly(vinyl alcohol), thylamide, sodium bicarbonate, sodium carbonate, starch derivatives, dextrin, beta cyclodextrin, dextrin derivatives, magnesium oxide, clays, bentonite and mixtures thereof.

The active ingredient of the present invention may be mixed with excipients which are pharmaceutically acceptable and compatible with the active ingredient and in amounts suitable for use in the therapeutic methods described herein. Various excipients may be homogeneously mixed with octreotide of the present invention as would be known to those skilled in the art. For example, octreotide may be mixed or combined with excipients such as but not limited to microcrystalline cellulose, colloidal silicon dioxide, lactose, starch, sorbitol, cyclodextrin and combinations of these.

Lubricants that are suitable for use in the pharmaceutical composition of the present invention include agents that act on the flowability of the powder to be compressed include but are not limited to silicon dioxide such as Aerosil 200, talc; stearic acid, magnesium stearate, calcium stearate, hydrogenated vegetable oils, sodium benzoate, sodium chloride, leucine carbowax, magnesium lauryl sulfate, and glyceryl monostearate.

According to another aspect of the invention, there is provided a stable, controlled-release implantable dosage formulation which includes an effective amount a octreotide in a hydrogel, and which, upon administration to a patient or as part of a therapy regimen, provides a release profile (of therapeutically effective blood plasma level of octreotide) extending for a period of at least about 2 months, preferably about 6 months, and up to about two years.

The dosage formulation of the present invention may comprise also one or more pharmaceutically acceptable excipients as mentioned above. In preferred embodiments, the dosage formulation will comprise diluents and a lubricant in addition to octreotide unit dose and the rate-controlling polymer. A particularly preferred excipient is magnesium stearate. When these materials are used, the magnesium stearate component preferably comprises from about 0.5 to about 5% w/w of the dosage formulation, more preferably about 2%, and the hydrogel and octreotide comprise the balance of the formulation.

Another preferred excipient is hydroxypropylcellulose. When used, the hydroxypropylcellulose component preferably comprises from about 0.5 to about 20% w/w of the dosage formulation, more preferably about 10%, and the hydrogel and octreotide comprise the balance of the formulation.

In a preferred embodiment, the formulation comprises both magnesium stearate and hydroxypropylcellulose, preferably about 2% magnesium stearate and about 10% hydroxypropylcellulose and the hydrogel and octreotide comprise the balance of the formulation.

As used herein, the term "controlled release" includes the predetermined, consistent release of active agent from the dosage formulation at a rate such that a therapeutically beneficial blood level below toxic levels of the active agent is maintained over a period of at least about 2 months, preferably about 6 months or more. Preferably, the amount of active agent in the implantable formulation establish a therapeutically useful plasma concentration through administration of the pharmaceutical composition every at least about two months, preferably about every six months, up to about two years.

The compositions of the present invention may be used for the treatment of hormonal diseases characterized by increased levels of GH and IGF-1 by administering to a patient an implantable formulation of the present invention. Preferably, the implant is administered every about six months, and releases a therapeutically effective amount of octreotide, preferably octreotide acetate. The implantable composition releases a concentration of octreotide in the patient at about the minimum therapeutically effective level to ameliorate the hormonal disorder, yet relatively lower compared to the maximum concentration in order to enhance restful periods for the patient during the day. The compositions may be administered to a subject at a dose and for a period sufficient to allow said subject to tolerate said dose without showing any adverse effects and thereafter increasing the dose of said active agent, if needed, at selected intervals of time until a therapeutic dose is achieved in the subject. For example, the active agent is preferably administered at a dose of from about 10 µg to about 1000 µg, preferably about 20 µg to about 800 µg, more preferably about 30 µg to about 300 µg, of octreotide daily for a period of at least about two months, more preferably about six months, up to about two years.

Compositions of the present invention where the octreotide is octreotide acetate are particularly suitable for use in the treatment of hormonal disorders which are characterized by increased levels of GH and IGF-1, more especially acromegaly. The octreotide acetate agent in accordance with the invention is also suitable for the treatment of symptoms associated with carcinoid syndrome and VIPomas.

As discussed above, prior to implantation, the implantable formulations may be hydrated or "primed" for a predetermined period of time. Suitable hydrating agents include, but are not limited to, water and other aqueous based solutions, including, but not limited to, saline and the like. The implantable formulations may be primed for less than one day up to a few months or longer. It has been observed that the step of priming affects the release of the active ingredient upon implantation. For example, priming enables the active ingredient to begin to infiltrate and saturate the walls of the hydrogel and potentially begin to leach out of the hydrogel prior to implantation depending upon the amount of time the implant is primed. A primed implant will begin to release active ingredient substantially upon implantation, and may result in a peak release of the drug shortly after implantation. In contrast, little to no priming may result in substantially no release of the active ingredient upon implantation for a period of time until the implant becomes hydrated and the active ingredient begins to be released.

In one embodiment, a method of administering a controlled release octreotide formulation comprises hydrating an octreotide formulation of the present invention for one month or less, preferably for one week or less and implanting into a patient.

In a further embodiment, a method of administering a controlled release octreotide formulation comprises implanting a dehydrated octreotide formulation of the present invention into a patient.

Additional features and embodiments of the present invention are illustrated by the following non-limiting examples.

Example 1

In Vitro Octreotide Release Rates

This example illustrates preparation of implantable octreotide formulations of the present invention and their in vitro release of octreotide. In the present study, a series of implants were tested to determine stability and in vitro release characteristics of octreotide from the hydrogel formulations over about 22 weeks (No. 146), 28 weeks (No. 136) and 33 weeks (all other formulations). Each implant contained about 50 milligrams of octreotide acetate and about 2% stearic acid, but the polymer cartridges contained different amounts of HEMA and HPMA and therefore exhibited different % EWCs, as depicted in Table 1.

TABLE 1

| Formulation Number | % HEMA | % HPMA | % EWC | Excipients/Other Ingredients |
|---|---|---|---|---|
| 146 | 0 | 99.5 | 22.9 | 2% stearic acid |
| 145 | 10 | 89.5 | 23.4 | 2% stearic acid |
| 147 | 15 | 84.5 | 24.4 | 2% stearic acid |
| 133 | 20 | 79.5 | 25.2 | 2% stearic acid |
| 144 | 25 | 74.5 | 25.6 | 2% stearic acid |
| 143 | 30 | 69.5 | 26.1 | 2% stearic acid |
| 142 | 35 | 64.5 | 26.6 | 2% stearic acid |
| 136 | 40 | 59.5 | 27.6 | 2% stearic acid |

Figure 2:
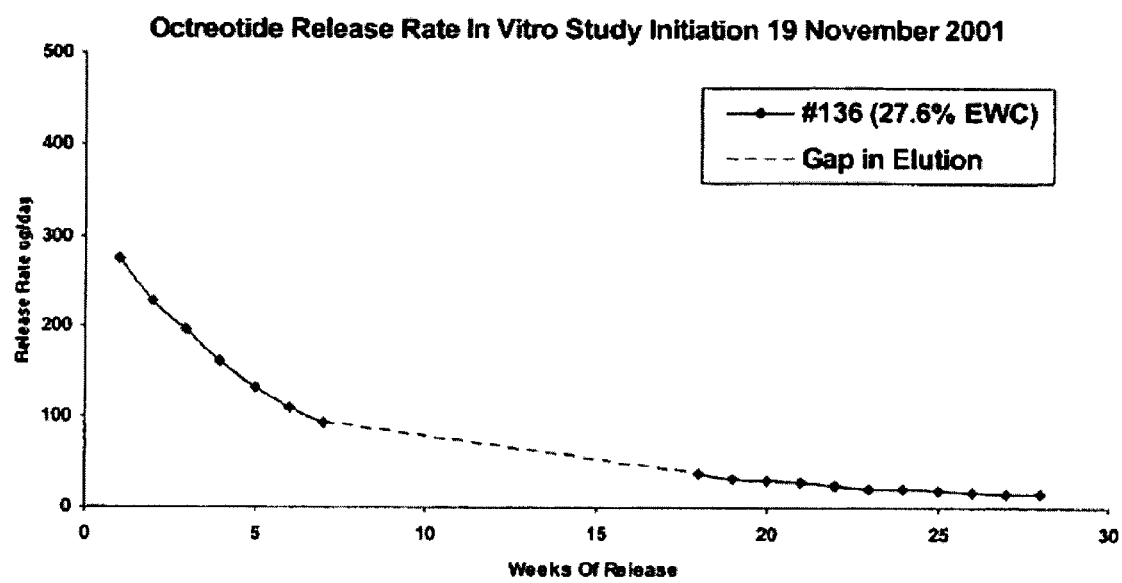
FIG. 2 is a graph showing the release of octreotide from an implant formulation of the present invention.
Figure 3:
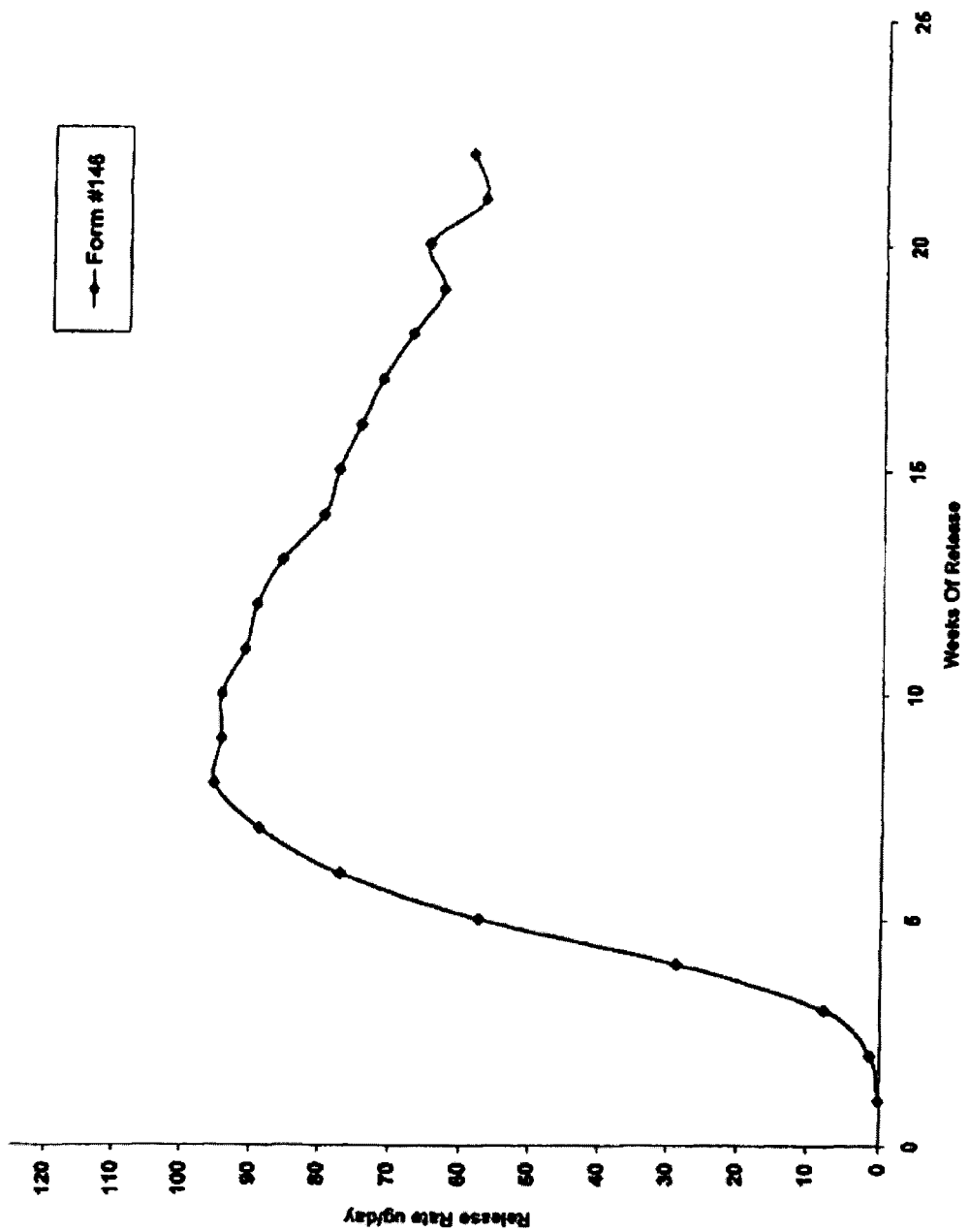
FIG. 3 is a graph showing the release of octreotide from an implant formulation of the present invention.
Figure 4:
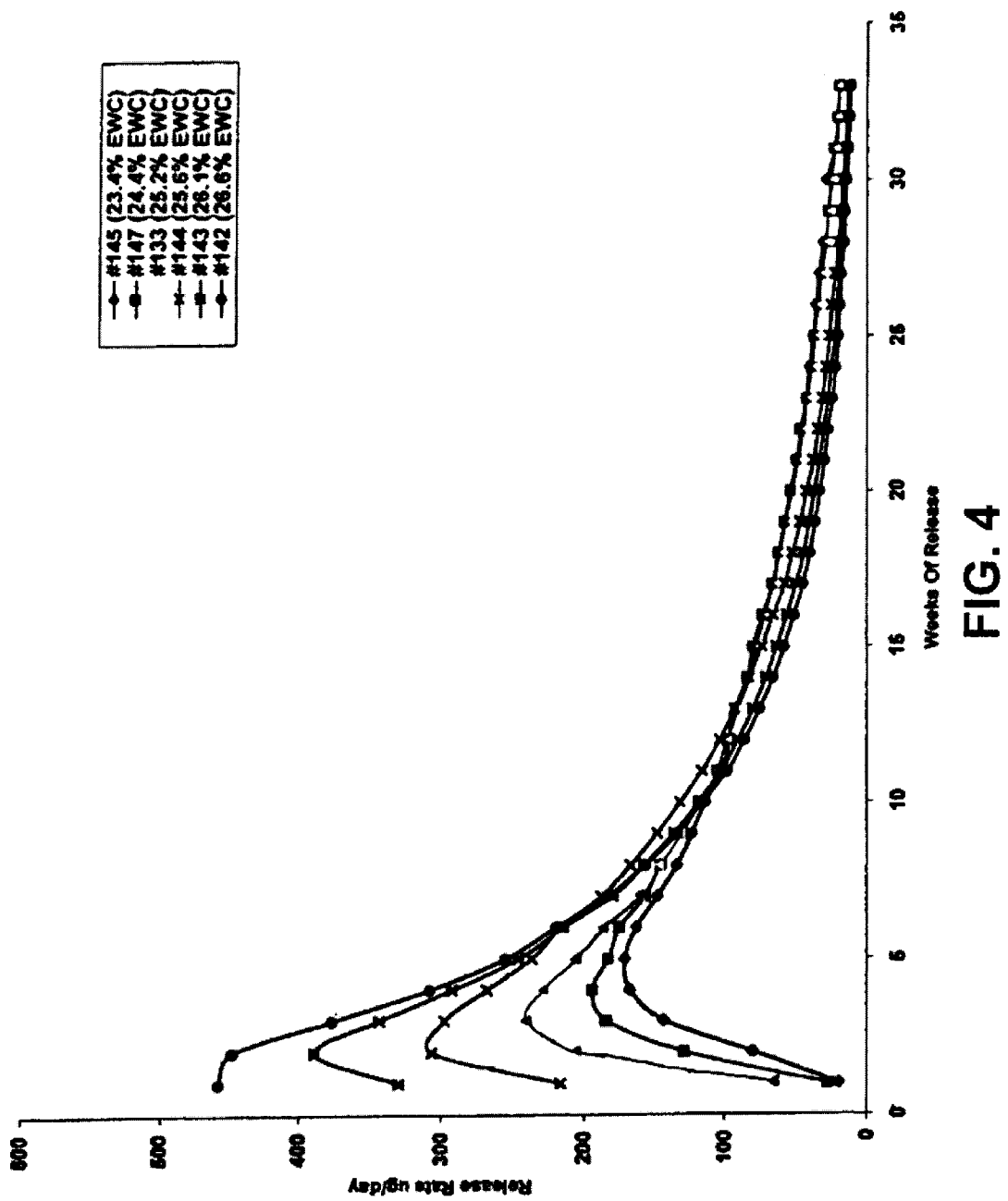
FIG. 4 is a graph showing the release of octreotide from six different implant formulations of the present invention.

FIGS. 2, 3 and 4 depict the release of octreotide from the implant per day for each of the formulations provided above. As noted in FIG. 2, the initial release was relatively high and dropped relatively quickly for Formulation No. 136. As shown in FIG. 3, the initial release rate for Formulation No. 146 was relatively low. FIG. 4 presents the release profiles for Formulation Nos. 145, 147, 133, 144, 143 and 142. As shown in FIG. 4, the initial release rates show a good relationship with the % EWC, ranging from 20 to 450 µg per day for % EWCs of 22.9 to 27.6%. However problems were encountered with respect to the osmotic pressure differential within the implant and the elution media. Therefore in order to stabilize the octreotide formulations a number of experiments were designed using excipients which would provide better stability based on a "preferential hydration" principle.

Example 2

Formulation Study in Calf Serum

To determine the effect of osmotic pressure on the swelling problem two implants of the present invention corresponding to Formulation No. 136 and Formulation No. 143 were eluted in calf serum. In particular, Formulation No. 136, composed of about 40% HEMA and 60% HPMA, containing octreotide acetate with 2% stearic acid and Formulation No. 143, composed of about 30% HEMA and 70% HPMA, containing a mixture of 20% PEG3300 and 80% octreotide acetate, were tested. After three months, the implants exhibited normal appearance, being relatively straight and only slightly swollen.

Example 3

Formulation Study

Due to osmotic pressure differential the implants described in example 1 were seen to swell significantly ultimately resulting in bursting of the implants. This example illustrates formulations designed to screen agents useful in stabilization of the octreotide implant. In the present study, a series of implants was monitored to determine the effect of excipient on implant shape and durability. Each of the polymer cartridges was composed of about 28% HEMA, about 66.5% HPMA and 5% glycerin. The contents contained octreotide acetate with various excipients, as shown in Table 2.

TABLE 2

| Sample No. | Excipients/Other Ingredients |
|---|---|
| 1 | None |
| 2 | 20% PEG 3300 |
| 3 | 40% PEG 3300 |
| 4 | 2% Stearic acid (control) |
| 5 | 10% Glycolic acid |
| 6 | 20% Poly(lactic acid) |
| 7 | 10% Mannitol |
| 8 | 10% MCC (microcrystalline cellulose) |
| 9 | 20% MCC |
| 10 | 10% Sesame oil |

Hydrophobic agents such as sesame oil and MCC separated in the formulation and did not provide "preferential hydration" and were less preferable in accordance with the present invention. Hydrophilic agents like PEG 3300 increased the osmotic pressure differential and increased swelling. Low molecular weight additives like mannitol and glycolic acid did not provide a stabilizing effect and resulted in a decrease in integrity. None of these agents provided satisfactory stabilization of the octreotide formulations. Therefore a second study, shown in Example 4, was initiated.

Example 4

Formulation Study and In Vitro Octreotide Release Rates

This study was conducted to evaluate stability of octreotide in hydrogel implants using various excipients as shown in Table 3. The excipients were chosen to have high molecular weight and some hydrophilic nature. Each implant was made from polymer cartridges composed of about 20% HEMA and about 80% HPMA. The appearance of the implants in saline was monitored and rated over the course of nine weeks. The results are shown in Table 3.

TABLE 3

| Formulation No. | Excipients/Other Ingredients | Implant Appearance at 9 Weeks (see key below) |
|---|---|---|
| 133 | 20% Dextran | 3 |
| 133 | 20% TPGS (vitamin E derivative) | 2 |
| 133 | 20% HEC (hydroxyethyl cellulose) | 3 |
| 133 | 20% HPC (hydroxypropyl cellulose) | 2 |
| 133 | 20% Albumin | 2 |
| 133 | 20% Pectin | 2 |
| 133 | 20% AcDiSol | 1.5 |
| 133 | 20% Carbopol | 1 |
| 133 | 2% SA (stearic acid) - control | 4 |

Figure 5:
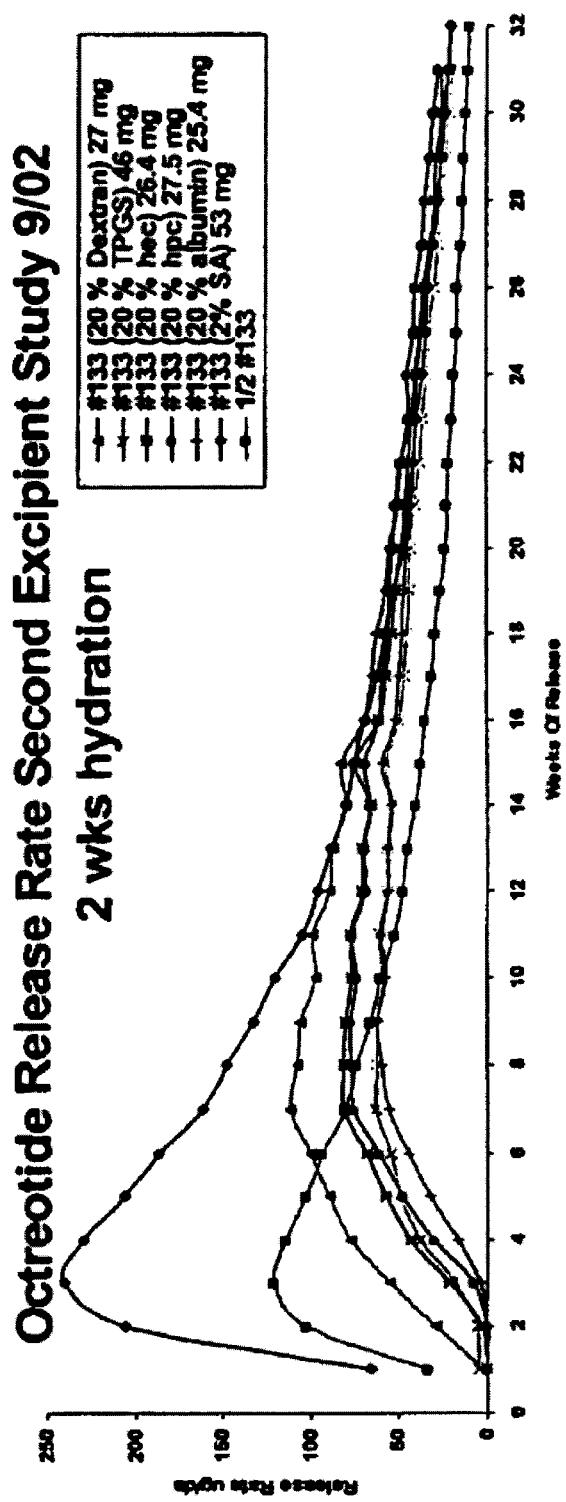
FIG. 5 is a graph showing the release of octreotide from different implant formulations of the present invention.

0-straight, no swelling, 1-straight with some swelling, 2- slight bending with some swelling 3- bent and swollen, 4- bent with significant deformation As depicted in FIG. 5, the formulation containing dextran had the highest elution rate. The formulations containing pectin, AcDiSol and Carbopol exhibited less than satisfactory release after two weeks hydration and nine weeks elution. Accordingly, a preferred embodiment having superior stabilizing effect, combination of good elution and appearance, was achieved with hydroxypropylcellulose.

Example 5

1-Month Implantation Study in a Healthy Dog

This example illustrates preparation of formulations of the present invention and their release of octreotide or pharmaceutically acceptable salts thereof. A healthy dog was implanted with one octreotide subdermal implant of the present invention. The octreotide subdermal implant formulation had a water content of 26.6%, containing 44 mg octreotide acetate. In vitro release rates were estimated at about 500 μg/day in week 1 and decreasing to about 300 μg/day in week 4 for a total release of about 10 mg of octreotide over the duration of the study. The implant was removed at 28 days after implantation. The implant used in this study was about 3.5 cm in length. Blood samples (1.5 ml) to obtain the serum concentration of octreotide acetate, IGF-1 and GH were obtained on days 0, 1-7, 11, 14, 18, 21, 25 and 28 via jugular puncture without anesthesia and without fasting.

Clinical observations included that the octreotide implant formulation was well tolerated, food intake was normal, and no abnormal behavior was noted.

Figure 6:
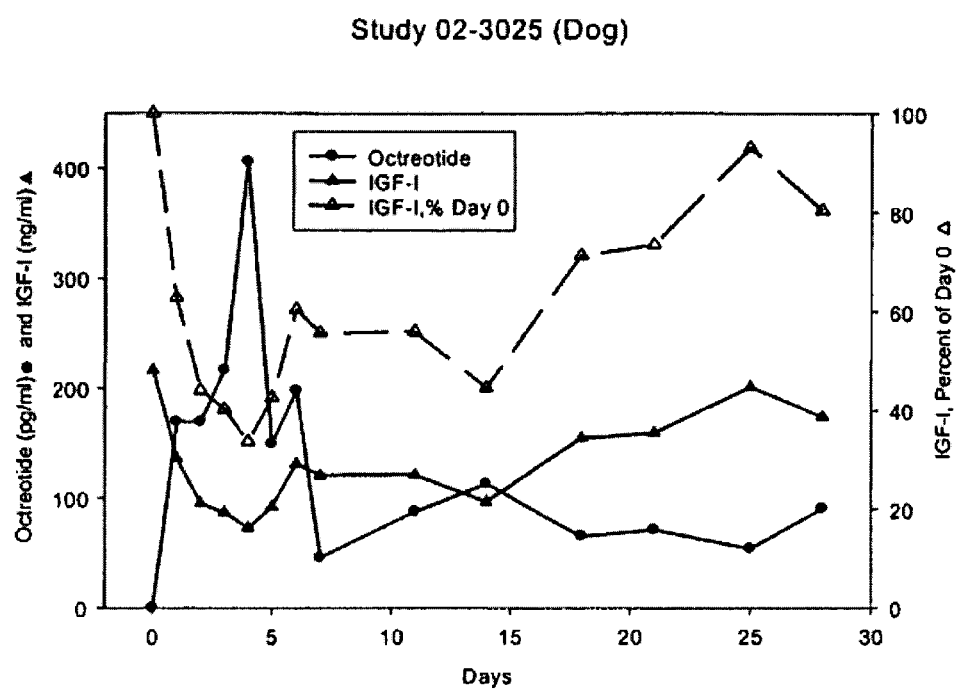
FIG. 6 is a graph showing octreotide and IGF-1 serum levels in a healthy dog implanted with an octreotide formulation of the present invention.

Serum analysis showed a peak of octreotide acetate at day 4 and detectable amounts of octreotide acetate at all intervals measured. IGF-1 concentrations decreased after implantation until day 4, then returned to predose levels by day 25. IGF-1 levels declined from 40 to 90% of pre-implantation level, as can be seen in FIG. 6.

Example 6

6-Month Implantation Study in Six Healthy Dogs

This example illustrates preparation of formulations of the present invention and their release of octreotide or pharmaceutically acceptable salts thereof. Six healthy dogs were divided into two groups and implanted with one or two octreotide subdermal implants of the present invention, respectively. The octreotide subdermal implants had a water content of about 25.2% and contained about 60 mg octreotide acetate. The implants were removed six months after implantation. Blood samples (10 ml) to obtain the serum concentration of octreotide acetate, IGF-1 and GH were obtained once daily for the first 7 days following implantation followed by twice a week sampling for three weeks, and then once a week until conclusion of the six month period. Four days prior to implantation, baseline serum samples were taken as a control.

Figure 7:
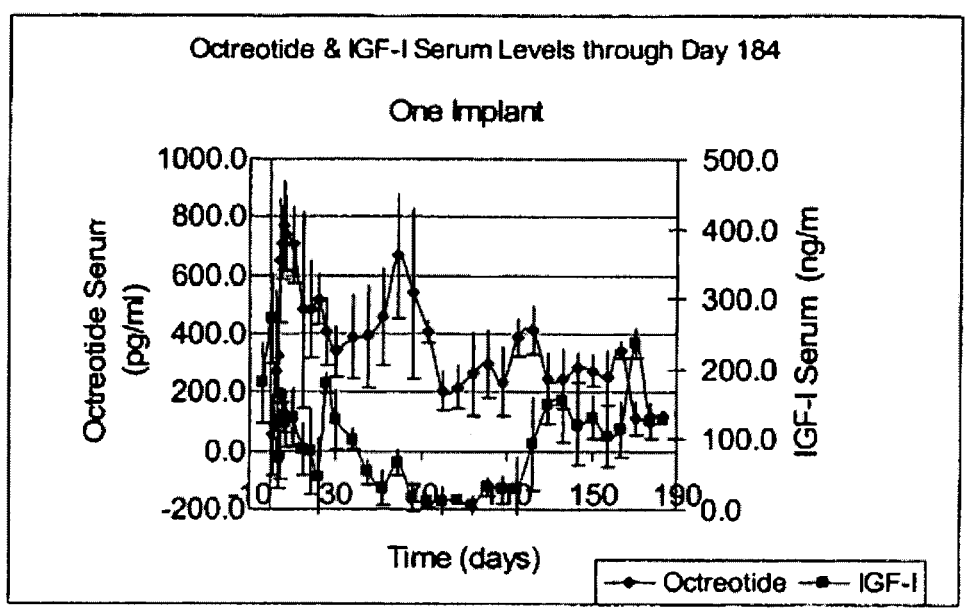
FIG. 7 is a graph showing octreotide and IGF-1 serum levels in a group of 3 healthy dogs implanted with one octreotide implant formulation of the present invention over a six month period.
Figure 8:
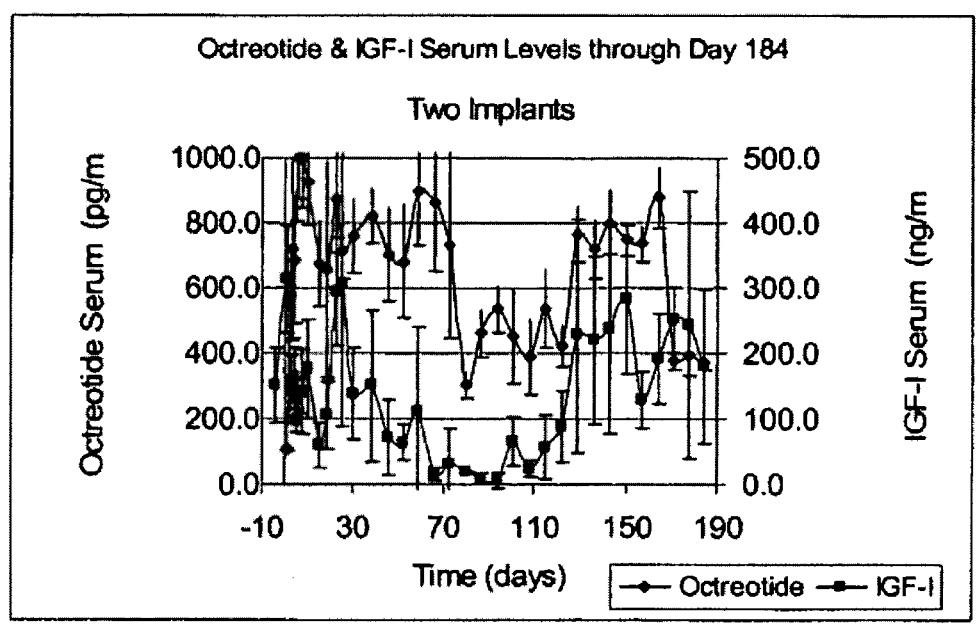
FIG. 8 is a graph showing octreotide and IGF-1 serum levels in a group of 3 healthy dogs implanted with two octreotide implant formulations of the present invention over a six month period.

Results indicate octreotide serum levels ranged from 200 to 700 pg/ml in dogs receiving one implant and 400 to 1000 pg/ml in dogs receiving two implants. IGF-1 levels were reduced as much as 90% in both treatment groups as can be seen in FIGS. 7 and 8. Measurement of serum GH levels was abandoned after about the first month of the study because levels in healthy animals are too low to detect further reductions. Clinical observations included the octreotide implant formulation was well tolerated, food intake was normal, and no abnormal behavior was noted.

Example 7

6-Month Implantation Study in Humans

This example illustrates preparation of formulations of the present invention and their release of octreotide or pharmaceutically acceptable salts thereof. A six-month study was conducted in eleven patients with acromegaly. One or two implants of the present invention were implanted subcutaneously in 11 patients diagnosed with acromegaly, who were previously treated with a commercially available octreotide LAR formulation. Levels of GH and IGF-1 were measured at baseline and every month thereafter for a period of six months. Each implant contained approximately 60 mg of octreotide acetate in a copolymer of 20% HEMA and 79.5% HPMA, with an EWC of about 25.2%. The implants used in this study were about 44 mm in length in a dry state and 50 mm in length in a hydrated state. The diameters of the implants were about 2.8 mm in a dry state and about 3.5 to about 3.6 mm in a hydrated state. The implants were hydrated for a period of about 1 week prior to implantation.

The reference ranges for GH is up to 2.5 mg/L, age-independent. Table 4, below, illustrates the basal levels of GH in mg/L over six months after implantation of octreotide implants of the present invention. Patient No. 11 did not participate in the study due to failure to meet screening criteria.

TABLE 4

| | | | | Basal GH Levels | | | | | | |
|---|---|---|---|---|---|---|---|---|---|---|
| Patient # | Age | # of Implants Received | Screening GH (mg/L) | Visit 1 (implant Insertion) Basal GH (mg/L) | Visit 2 (Month 1) Basal GH (mg/L) | Visit 3 (Month 2) Basal GH (mg/L) | Visit 4 (Month 3) Basal GH (mg/L) | Visit 5 (Month 4) Basal GH (mg/L) | Visit 6 (Month 5) Basal GH (mg/L) | Visit 7 (Month 6) Basal GH (mg/L) |
| 001 | 39 | 1 | 26 | 16.3 | 0.9 | 1.5 | 1.1 | 1.1 | 1.1 | 2.1 |
| 002 | 38 | 2 | 17.8 | 20.7 | 1.4 | 0.2 | 0.3 | 0.2 | 0.3 | 0.48 |
| 003 | 49 | 1 | 67 | 55 | 2.8 | 3.1 | 3.3 | 5.0 | 5.3 | 5.8 |
| 004 | 47 | 2 | 7.9 | 7 | 2.6 | 3.8 | 2.8 | 3.7 | 4.0 | 2.4 |
| 005 | 43 | 1 | 10.8 | 11 | 2.2 | 1.8 | 2.2 | 1.6 | 2.2 | 1.3 |
| 006 | 43 | 1 | 1.7 | 1.7 | 1.8 | 2.3 | 1.9 | 1.7 | 1.8 | 1.9 |
| 007 | 30 | 2 | 23.3 | 21.8 | 2.4 | 2.2 | 2.9 | 2.0 | 1.1 | 0.51 |
| 008 | 58 | 2 | 1.9 | 3.2 | 0.1 | 0.1 | 2.0 | 0.1 | 0.6 | 0.11 |
| 009 | 47 | 2 | 14.9 | 14.1 | 1.4 | 0.9 | 1.5 | 1.1 | 1.4 | 1.4 |
| 010 | 78 | 1 | 4 | 5.2 | 0.4 | 0.2 | 0.5 | 0.2 | 0.3 | 1.0 |
| 012 | 40 | 2 | 21.1 | 27.8 | 13.5 | 13.7 | 14 | 11.9 | 8.9 | 13.1 |
| mean | | | | 16.7 | 2.7 | 2.7 | 3.0 | 2.6 | 2.7 | 2.7 |

As shown above, by month six 89% of subjects exhibited normalized growth hormone levels.

Reference ranges for IGF-1 is as follows: (i) 17-24 years old is about 180-780 ng/mL; (ii) 25-39 years old is about 114-400 ng/mL; (iii) 40-54 years old is about 90-360 ng/mL; and (iv) >54 years old is about 70-290 ng/mL. Table 5, below, illustrates the basal levels of IGF-1 in ng/ml over six months after implantation of octreotide implants of the present invention.

TABLE 5

Serum levels of IGF-1

| Patient # | Age | # of Implants Received | Screening IGF-1 (ng/mL) | Visit 1 (implant Insertion) IGF-1 (ng/mL) | Visit 2 (Month 1) IGF-1 (ng/mL) | Visit 3 (Month 2) IGF-1 (ng/mL) | Visit 4 (Month 3) IGF-1 (ng/mL) | Visit 5 (Month 4) IGF-1 (ng/mL) | Visit 6 (Month 5) IGF-1 (ng/mL) | Visit 7 (Month 6) IGF-1 (ng/mL) |
|---|---|---|---|---|---|---|---|---|---|---|
| 001 | 39 | 1 | 1500 | 1500 | 820 | 600 | 900 | 880 | 790 | 750 |
| 002 | 38 | 2 | 1700 | 1300 | 210 | 180 | 190 | 170 | 130 | 230 |
| 003 | 49 | 1 | 1100 | 1200 | 610 | 550 | 750 | 660 | 850 | 660 |
| 004 | 47 | 2 | 1700 | 1800 | 1100 | 1200 | 1200 | 1100 | 910 | 990 |
| 005 | 43 | 1 | 1100 | 1000 | 450 | 510 | 480 | 600 | 490 | 430 |
| 006 | 43 | 1 | 520 | 580 | 470 | 430 | 440 | 480 | 440 | 460 |
| 007 | 30 | 2 | 1900 | 1700 | 440 | 560 | 560 | 600 | 430 | 520 |
| 008 | 58 | 2 | 1700 | 1200 | 220 | 240 | 170 | 260 | 160 | 240 |
| 009 | 47 | 2 | 2200 | 1800 | 590 | 830 | 950 | 930 | 1100 | 1100 |
| 010 | 78 | 1 | 590 | 490 | 270 | 260 | 230 | 310 | 220 | 350 |
| 012 | 40 | 2 | 1600 | 1600 | 1300 | 1500 | 1400 | 1700 | 1500 | 1400 |
| mean | | | | 1288 | 589 | 624 | 661 | 699 | 602 | 648 |

As shown above, by month six, 22% of subjects exhibited a normalized IGF-1 level.

Figure 9A:
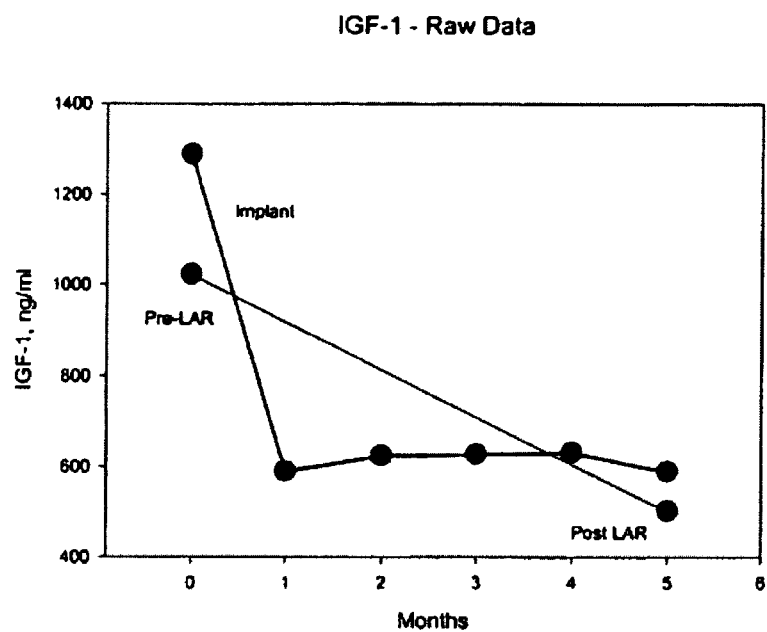
FIGS. 9A and 9B are graphs depicting the IGF-1 serum level and percent change in eleven human subjects with acromegaly over six months implanted with an octreotide formulation of the present invention, respectively.
Figure 9B:
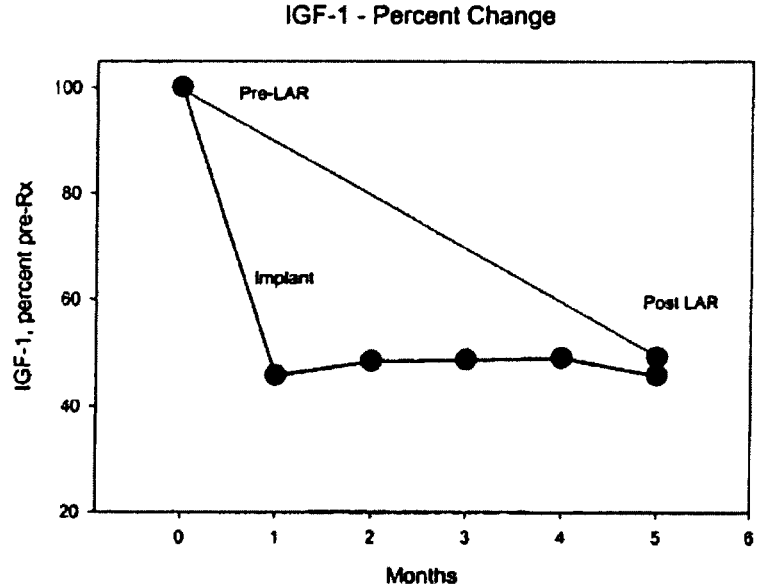

FIGS. 9A and 9B demonstrate a comparison of the octreotide implant of the present invention with a commercially available formulation of octreotide acetate and the efficacy of the implant appeared to be at least as good as that of the commercially available octreotide LAR formulation. The therapeutic effect of these implants continued successfully for the entire 6 months of the study duration.

IGF-1 levels were decreased in all patients, with normalization in 2 patients. The decrease was already observed at one month of therapy and the mean IGF-1 level was stable for the following 5 months. A comparison with decreases previously observed in the same patients while on the commercially available octreotide LAR formulation therapy was possible in 8 of the 9 patients. In 6 of the 8 patients, the percentage decrease in IGF-1 during the implant was greater than that while on the commercially available octreotide LAR formulation, whereas in 2, it was less. After 6 months of therapy with the implant, GH levels in 3 patients were <1 ng/ml and in another 5, were <2.5 ng/ml. This compared favorably with the results on the commercially available octreotide LAR formulation, where GH levels in only 2 patients were <1 ng/ml and in another 2, were under 2.5 ng/ml.

Levels of octreotide in the serum of patients was also measured, as shown in Table 6, below.

TABLE 6

Octreotide Serum Levels

| | | Month | | | | | | | |
|---|---|---|---|---|---|---|---|---|---|
| #Implants | Patient ID | 1 Visit 2 | 2 Visit 3 | 3 Visit 4 | 4 Visit 5 | 5 Visit 6 | 6 Visit 7 | 7 Visit 8 | Gender |
| 1 | Patient 1 | 1181 | 874.5 | 738.0 | 894.3 | 699.2 | 722.3 | 169.0 | F |
| 2 | Patient 2 | 2686 | 2478 | 1625 | 1833 | 1388 | 1203 | 280 | M |
| 1 | Patient 3 | 2570 | 2351 | 1332 | 980.5 | 1131 | 775.2 | 173 | F |
| 2 | Patient 4 | 4268 | 3308 | 2582 | 2650 | 2455 | 1984 | 166 | M |
| 1 | Patient 5 | 1218 | 1022 | 610.0 | 783.2 | 709.4 | 545.8 | 144 | F |
| 1 | Patient 6 | 1899 | 1445 | 1427 | 1123 | 1148 | 747.7 | 206 | F |
| 2 | Patient 7 | 5524 | 2621 | 3656 | 3141 | 2205 | 1466 | 154 | F |
| 2 | Patient 8 | 8684 | 3387 | 4899 | 3336 | 3454 | 1765 | 170 | F |
| 2 | Patient 9 | 3850 | 860.6 | 2638 | 1766 | 1729 | 1510 | 203 | M |

TABLE 6-continued

Octreotide Serum Levels

| | | Month | | | | | | | |
|---|---|---|---|---|---|---|---|---|---|
| | | 1 | 2 | 3 | 4 | 5 | 6 | 7 | |
| #Implants | Patient ID | Visit 2 | Visit 3 | Visit 4 | Visit 5 | Visit 6 | Visit 7 | Visit 8 | Gender |
| 1 | Patient 10 | 2055 | 1628 | 1192 | 863.9 | 1641 | 1231 | 1130 | F |
| 2 | Patient 12 | 2527 | 1366 | 2006 | 962.8 | 1484 | 1156 | 189 | M |

*Patient 10 did not have the implant removed at visit 7

Figure 10:
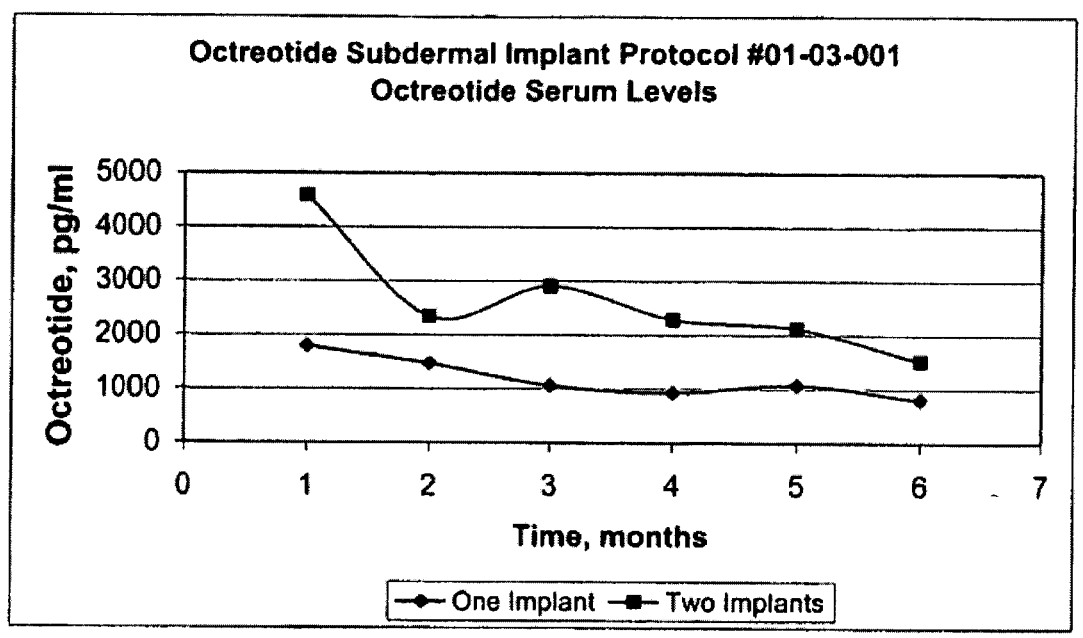
FIG. 10 is a graph depicting octreotide serum levels in eleven human subjects with acromegaly over six months implanted with an octreotide formulation of the present invention.

A comparison of the octreotide levels achieved with one and two implants is depicted in the graph in FIG. 10.

Overall, results indicated that the octreotide implant of the present invention is at least as effective as the commercially available LAR formulation of octreotide acetate in reducing GH levels and IGF-1 levels in patients with acromegaly.

Example 8

This example illustrates preparation of formulations of the present invention and their release of octreotide or pharmaceutically acceptable salts thereof. Two healthy dogs were implanted with one octreotide subdermal implant of the present invention. The implants were not hydrated prior to implantation. The octreotide subdermal implants were composed of about 59.5% HPMA and about 40% HEMA and had an equilibrium water content of about 27.6%. The implants contained about 84 mg of octreotide acetate, hydroxypropylcellulose and magnesium stearate. The implants were removed 6 months after implantation. Blood samples (10 ml) to obtain the serum concentration of octreotide acetate and IGF-1 were obtained once daily every other day for the first four weeks following implantation followed by twice a week sampling for four weeks, and then once a week until conclusion of the 6 month period. Two days prior to implantation, baseline serum samples were taken as a control.

Figure 11:
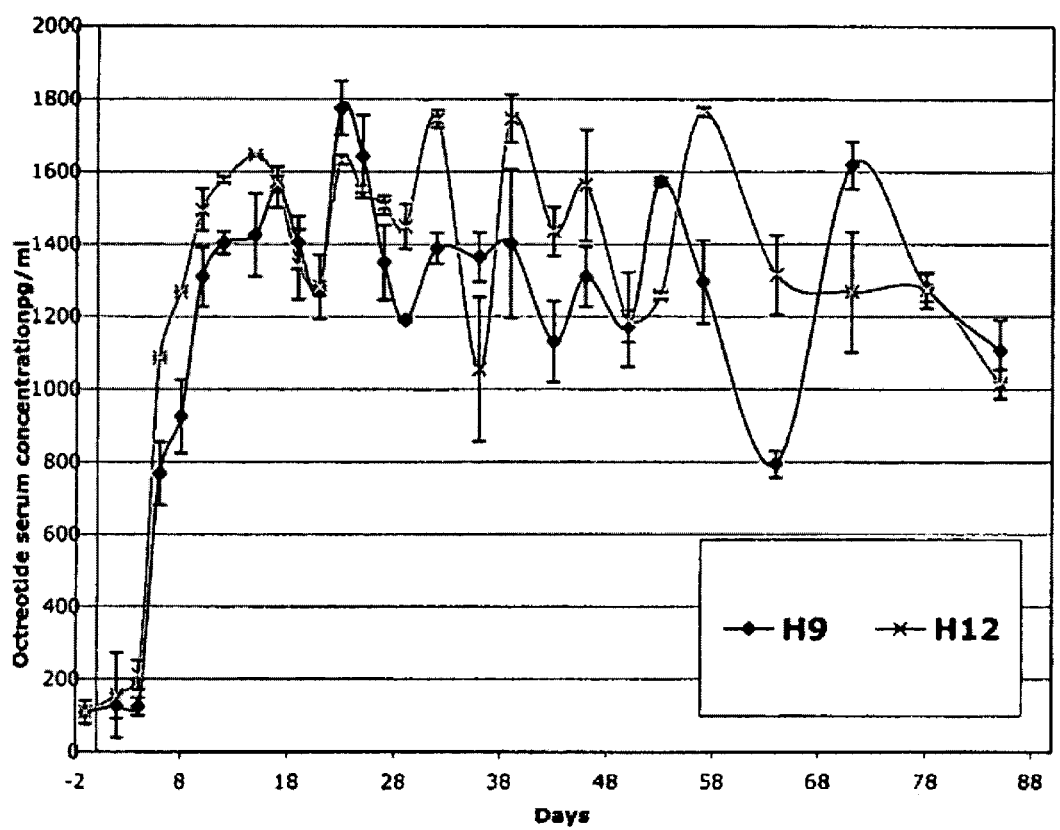
FIG. 11 is a graph depicting octreotide serum levels in two dogs over six months implanted with an octreotide formulation of the present invention.
Figure 12:
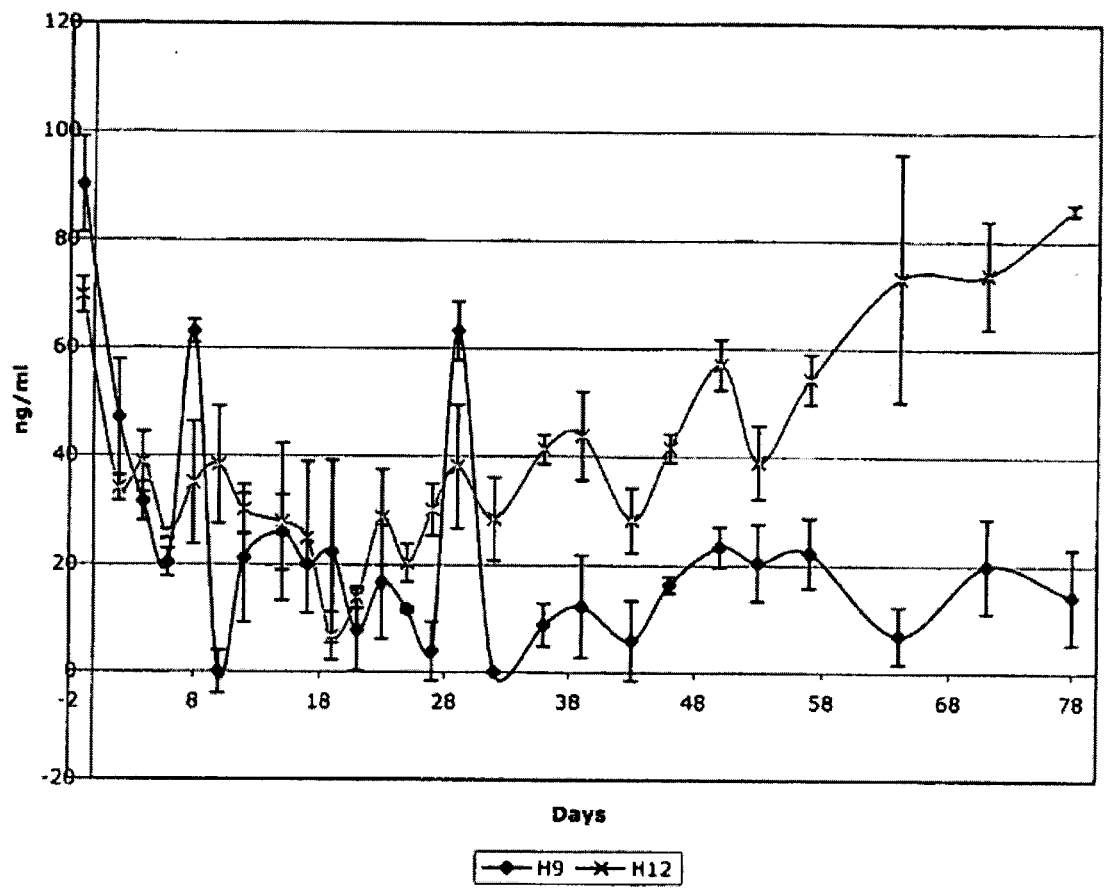
FIG. 12 is a graph depicting IGF-1 serum levels in two dogs over six months implanted with an octreotide formulation of the present invention.

FIG. 11 shows the octreotide levels in the serum of the dogs and FIG. 12 shows the levels of IGF-1 in the dogs.

Although the present invention has been described in considerable detail with reference to certain preferred embodiments thereof, other versions are possible. Therefore the spirit and scope of the appended claims should not be limited to the description and the preferred versions contain within this specification.

The invention claimed is:

1. A method of treating a patient suffering from overproduction of growth hormone or IGF-1, said method comprising:
   implanting subcutaneously into a patient in need thereof at least one implant comprising a hydrogel and a pharmaceutical formulation comprising octreotide;
   wherein said pharmaceutical formulation is contained within said hydrogel, which hydrogel comprises a copolymer obtained from the copolymerization of a mixture comprising at least two hydrophilic, ethylenically unsaturated monomers;
   wherein said pharmaceutical formulation contains between about 20 to about 150 milligrams of octreotide, in free form or salt form;
   wherein said pharmaceutical formulation further comprises hydroxypropylcellulose; and
   wherein said at least one implant releases a therapeutically effective amount of said octreotide to said patient over a period of at least about two months.

2. The method of claim 1, wherein said effective amount of said octreotide provides an in vivo average $C_{SS}$ in said patient of about 0.1 ng/ml to about 9 ng/ml of octreotide.

3. The method of claim 1, wherein said pharmaceutical formulation contains from about 40 to about 90 milligrams of octreotide.

4. The method of claim 1, wherein said octreotide is octreotide acetate.

5. The method of claim 4, wherein said pharmaceutical formulation contains about 50 milligrams of said octreotide acetate.

6. The method of claim 4, wherein said pharmaceutical formulation contains about 80 milligrams of said octreotide acetate.

7. The method of claim 2, wherein said effective amount of said octreotide provides an in vivo average $C_{SS}$ in said patient of about 1 ng/ml to about 2 ng/ml of octreotide.

8. The method of claim 1, wherein said at least one implant releases a therapeutically effective amount of octreotide over a period of about two months to about two years.

9. The method of claim 1, wherein said at least one implant releases a therapeutically effective amount of said octreotide over about six months.

10. The method of claim 1, wherein said at least two hydrophilic, ethylenically unsaturated monomers are 2-hydroxyethyl methacrylate and hydroxypropyl methacrylate.

11. The method of claim 1, wherein said copolymer comprises about 20% of 2-hydroxyethyl methacrylate and about 80% hydroxypropylmethacrylate.

12. The method of claim 1, wherein the pharmaceutical formulation contains about 0.5 to 20% w/w of the hydroxypropylcellulose.

13. The method of claim 1, wherein said pharmaceutical formulation further comprises magnesium stearate.

14. The method of claim 13, wherein the pharmaceutical formulation contains about 0.5 to 5% w/w of the magnesium stearate.

15. The method of claim 1, wherein said at least one implant releases said octreotide at a rate of about 10 µq to about 1000 µg per day over a period of about six months.

16. The method of claim 1, wherein said at least one implant is two or more implants.

17. The method of claim 1, wherein said at least one implant releases said octreotide at a rate of about 30 µg to about 250 µg per day in vitro.

18. The method of claim 1, wherein the at least one implant is implanted in a dry state.

19. The method of claim 1, wherein the at least one implant is implanted in a hydrated state.

20. The method of claim 1, wherein said copolymer comprises about 40% of 2-hydroxyethyl methacrylate and about 60% hydroxypropylmethacrylate.

* * * * *